US012577621B2

(12) United States Patent
Andolina et al.

(10) Patent No.: US 12,577,621 B2
(45) Date of Patent: Mar. 17, 2026

(54) LRRK2 MUTATIONS AS BIOMARKERS FOR THE PREDICTION OF IMMUNE CHECKPOINT RESPONSE IN CANCER

(71) Applicant: Duke University, Durham, NC (US)

(72) Inventors: Laurie Andolina, Durham, NC (US); Edgardo Parrilla Castellar, Durham, NC (US)

(73) Assignee: Duke University, Durham, NC (US)

( * ) Notice: Subject to any disclaimer, the term of this patent is extended or adjusted under 35 U.S.C. 154(b) by 535 days.

(21) Appl. No.: 17/469,507

(22) Filed: Sep. 8, 2021

(65) Prior Publication Data

US 2022/0073997 A1     Mar. 10, 2022

Related U.S. Application Data

(60) Provisional application No. 63/075,348, filed on Sep. 8, 2020.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
CPC ............ C12Q 1/6886; C12Q 2600/106; C12Q 2600/156
See application file for complete search history.

(56) References Cited

U.S. PATENT DOCUMENTS

| | | |
|---|---|---|
| 3,710,795 A | 1/1973 | Higuchi et al. |
| 4,863,457 A | 9/1989 | Lee |
| 5,501,856 A | 3/1996 | Ohtori et al. |
| 6,682,736 B1 | 1/2004 | Hanson et al. |
| 6,984,720 B1 | 1/2006 | Korman et al. |
| 7,488,802 B2 | 2/2009 | Collins et al. |
| 7,605,238 B2 | 10/2009 | Korman et al. |
| 8,552,156 B2 | 10/2013 | Takayanagi et al. |
| 8,841,418 B2 | 9/2014 | Karsunky et al. |
| 8,907,053 B2 | 12/2014 | Sasikumar et al. |
| 9,422,339 B2 | 8/2016 | Sasikumar et al. |
| 9,605,070 B2 | 3/2017 | Sabatos-Peyton et al. |
| 9,631,026 B2 | 4/2017 | Karsunky et al. |

(Continued)

FOREIGN PATENT DOCUMENTS

| | | | |
|---|---|---|---|
| CN | 105861708 A | * | 8/2016 |
| EP | 0430539 A2 | | 6/1991 |

(Continued)

OTHER PUBLICATIONS

Wu et al., "Genetic Variants of LRRK2 in Taiwanese Parkinson's Disease," 2013. PLoS One, vol. 8, Issue 12, e82001. (Year: 2013).*

(Continued)

*Primary Examiner* — Angela M. Bertagna
*Assistant Examiner* — Francesca Filippa Giammona
(74) *Attorney, Agent, or Firm* — Kilpatrick Townsend & Stockton L.L.P.

(57) ABSTRACT

The present disclosure describes methods and compositions involving using LRRK2 mutations as biomarkers for the prediction of immune checkpoint response in cancer and methods and compositions for treating cancers having certain LRRK2 mutations in a subject.

12 Claims, 5 Drawing Sheets

Specification includes a Sequence Listing.

Case 2

Case 3

Case 4

Case 8

(56) References Cited

U.S. PATENT DOCUMENTS

| | | | | |
|---|---|---|---|---|
| 2006/0068433 A1* | 3/2006 | Godfrey | ............... | C12Q 1/6851 435/6.1 |
| 2008/0241223 A1 | 10/2008 | Nivaggioli et al. | | |
| 2016/0257749 A1 | 9/2016 | Lifke et al. | | |

FOREIGN PATENT DOCUMENTS

| | | | | | |
|---|---|---|---|---|---|
| EP | 0488401 A1 | 6/1992 | | | |
| EP | 3041822 B1 | 8/2017 | | | |
| WO | 2015034820 A1 | 3/2015 | | | |
| WO | 2016142833 A1 | 9/2016 | | | |
| WO | 2016144803 A2 | 9/2016 | | | |
| WO | WO-2018209315 A1 * | 11/2018 | ........... | A61K 35/768 | |

OTHER PUBLICATIONS

Machine Translation of CN-105861708-A. Obtained Dec. 29, 2023. (Year: 2016).*

Agalliu et al., "Cancer Outcomes Among Parkinson's Disease Patients with Leucine Rich Repeat Kinase 2 Mutations, Idiopathic Parkinson's Disease Patients, and Nonaffected Controls," 2019. Movement Disorders. vol. 34, Issue 9, pp. 1392-1398. (Year: 2019).*

Nichols et al., "Substrate specificity and inhibitors of LRRK2, a protein kinase mutated in Parkinson's disease," Biochem. J., vol. 424, pp. 47-60. (Year: 2009).*

Kim et al., "Identification of Somatic Mutations in Dementia-related Genes in Cancer Patients," Current Alzheimer Research, vol. 17, pp. 835-844. Available Online Aug. 2020 (see supplied Online Information). (Year: 2020).*

Zong et al., "Expression of the immune checkpoint VISTA in breast cancer," Immunotherapy, vol. 69, pp. 1437-1446. (Year: 2020).*

"Broad Institute TCGA Genome Data Analysis Center Mutation Analysis (MutSigCV v0.9)", Broad Institute of MIT and Harvard, doi:10.7908/C1PK0FH7, 2016, 20 pages.

Altschul et al., "Basic Local Alignment Search Tool", Journal of Molecular Biology, vol. 215, No. 3, Oct. 5, 1990, pp. 403-410.

Altschul et al., "Gapped BLAST and PSI-BLAST: A New Generation of Protein Database Search Programs", Nucleic Acids Research, vol. 25, No. 17, Sep. 1, 1997, pp. 3389-3402.

Berge et al., "Pharmaceutical Salts", Journal of Pharmaceutical Sciences, vol. 66, No. 1, Jan. 1977, pp. 1-19.

Castellar et al., "Somatic Mutations in LRRK2 Identify a Subset of Invasive Mammary Carcinomas Associated with High Mutation Burden", The American Journal of Pathology, vol. 190, No. 12, Dec. 2020, pp. 2478-2482.

Jaleel et al., "LRRK2 Phosphorylates Moesin at Threonine-558: Characterization of How Parkinson's Disease Mutants Affect Kinase Activity", Biochemical Journal, vol. 405, Jul. 15, 2007, pp. 307-317.

Karlin et al., "Applications and Statistics for Multiple High-Scoring Segments in Molecular Sequences", Proceedings of the National Academy of Sciences USA, vol. 90, No. 12, Jun. 15, 1993, pp. 5873-5877.

Li et al., "Design and Synthesis of Paclitaxel Conjugated with an ErbB2-Recognizing Peptide, EC-1", Biopolymers, vol. 87, No. 4, Nov. 2007, pp. 225-230.

Liu et al., "Synthesis of 2'-Paclitaxel Methyl 2-Glucopyranosyl Succinate for Specific Targeted Delivery to Cancer Cells", Bioorganic & Medicinal Chemistry Letters, vol. 17, No. 3, Mar. 2007, pp. 617-620.

Myasnikov et al., "Structural Analysis of the full-Length Human LRRK2", Cell, vol. 184, No. 13, Jun. 24, 2021, pp. 3519-3527.

Needleman et al., "A General Method Applicable to the Search for Similarities in the Amino Acid Sequence of Two Proteins", Journal of Molecular Biology, vol. 48, No. 3, Mar. 1970, pp. 443-453.

Pearson et al., "Improved Tools for Biological Sequence Comparison", Proceedings of the National Academy of Sciences of the United States of America, vol. 85, No. 8, Apr. 1988, pp. 2444-2448.

Smith et al., "Comparison of Biosequences", Advances in Applied Mathematics, vol. 2, No. 4, Dec. 1981, pp. 482-489.

Wang et al., "Selection of PD1/PD-L1 X-Aptamers", Biochimie, vol. 145, Feb. 2018, pp. 125-130.

Aggarwal, C., et al., Assessment of Tumor Mutational Burden and Outcomes in Patients With Diverse Advanced Cancers Treated With Immunotherapy. Jama Netw Open. 2023;6[5]:e2311181; doi: 10.1001/jamanetworkopen.2023.11181.

U.S. Food and Drug Administration Premarket Approval for FoundationOne CDx (PMA No. P170019, Supplement No. S016), Decision Granted Jun. 16, 2020, available at www.accessdata.fda.gov/scripts/cdrh/cfdocs/cfpma/pma.cfm?id=P170019S016.

* cited by examiner

Case 2     Case 3     Case 4     Case 8

FIG. 2

LRRK2 MUTATIONS AS BIOMARKERS FOR THE PREDICTION OF IMMUNE CHECKPOINT RESPONSE IN CANCER

PRIOR RELATED APPLICATION

This application claims the benefit of and priority to U.S. Provisional Application No. 63/075,348, filed on Sep. 8, 2020, which is hereby incorporated by reference in its entirety.

SEQUENCE LISTING

The official copy of the sequence listing is submitted electronically via EFS-Web as an ASCII formatted sequence listing with a file named 106707-1266919-DU6704US_SL.txt, created on Oct. 26, 2021, and having a size of 30,520 bytes. The sequence listing contained in this ASCII formatted document is part of the specification and is herein incorporated by reference in its entirety.

FIELD

This disclosure describes compositions and methods for treating cancer.

BACKGROUND

Cancer and Parkinson's disease (PD), the most common movement neurodegenerative disorder, at first glance seem pathophysiologically dissimilar. Whereas cancer results from an uncontrolled regenerative process, PD is characterized by neuronal cell death. Although these disease processes appear to be mechanistically contradictory, an association between PD and cancer has been established, suggesting overlap in the underlying biochemical dysfunction. Studies have shown both increases and decreases in cancer incidence among PD subjects, depending on the cancer type and whether or not PD was familial or idiopathic. Interestingly, breast cancer is consistently observed to be increased among PD subjects compared to controls.

Mutations in the leucine rich repeat kinase 2 (LRRK2) gene are the most common cause of familial PD and, like idiopathic PD, carriers of LRRK2 mutations are at increased risk for breast cancer. Among the subset of PD patients with a LRRK2 mutation, cancer may arise before a PD diagnosis, suggesting that this may be the sentinel event in at least a subset of LRRK2 mutation carriers. Despite this observation, the link between LRRK2 mutations and breast cancer has been largely unexplored.

BRIEF SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the findings by the inventors of the presence of somatic LRRK2 mutations in cancers, such as breast cancer, and that this subset of tumors displays high-risk features with a high mutation burden, making them promising candidates for immune checkpoint therapy.

Accordingly, one aspect of the present disclosure provides a method of determining whether a cancer in a subject is responsive to immune checkpoint inhibitor therapy and treating the subject if said determination is made, the method comprising, consisting of, or consisting essentially of: (a) obtaining a biological sample from the subject; (b) determining the presence or absence of at least one LRRK2 mutation as provided herein; and (c) administering to the subject an immune checkpoint therapy if at least one LRRK2 mutation as provided herein is present.

In some embodiments, the one or more LRRK2 mutations is located in one or more domains of the LRRK2 protein: the Armadillo domain, the inter-domain, the leucine-rich repeat ROC domain, the kinase domain, or the WD40 domain. In some embodiments, the one or more LRRK2 mutations are one or more of a missense mutation, a frameshift mutation, or a nonsense mutation.

In some embodiments, the LRRK2 mutations comprise at least one mutation as provided in Table 1. In some embodiments, the one or more LRRK2 mutations do not comprise any of the mutations as provided in Table 2. In some embodiments, the one or more LRRK2 mutations do not comprise any of the mutations: p.N1437H, p.R1441C/G/H, p.Y1699C, p.S1761R, p.G2019S, p.I2012T, and p.I2020T mutations.

In some embodiments, the cancer comprises breast cancer.

In some embodiments the immune checkpoint therapy is administering an PD-1 inhibitor or an PD-L1 inhibitor. In some embodiments the immune checkpoint therapy is administering a CTLA-4 inhibitor. In some embodiments, immune checkpoint therapy is administering a TIM3 inhibitor.

In another embodiment, the method further provides administering one or more additional therapies. In some embodiments, the additional therapy is one or more of chemotherapy, radiation, surgery, or any combinations thereof.

In one embodiment, the at least one additional therapy is administered prior the immune checkpoint therapy. In another embodiment, the at least one additional therapy is administered concurrently with the immune checkpoint therapy. In yet another embodiment, the at least one additional therapy is administered after the immune checkpoint therapy. In other embodiments, LRRK2 may serve as a drug target for breast (and potentially) other cancers.

Another aspect of the present disclosure provides a kit for treating a subject having cancer, the kit comprising: (1) primers for detecting one or more LRRK2 mutations in a biological sample, wherein the one or more LRRK2 mutations result in reduction in kinase activity of LRRK2 as compared to the wild type LRRK2 and (2) instructions for identifying the one or more LRRK mutations. In some embodiments, the one or more LRRK2 mutation results in reduced kinase activity of the LRRK2, and wherein one or more LRRK2 mutations is located in one or more domains of the LRRK2 protein: the Armadillo domain, the inter-domain, the leucine-rich repeat ROC domain, the kinase domain, or the WD40 domain.

Another aspect of the present disclosure provides all that is described and illustrated herein.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A. Abundant granular eosinophilic cytoplasm, with mitochondrial-rich apocrine-like features, prevailed in LRRK2-mutated tumors (magnification is 200×). FIG. 1B. Box-plot of non-silent mutations per megabase of DNA in tumors with LRRK2 mutations (N=16) compared to the BRCA-TCGA cohort (N=972), including cases with no LRRK2 mutations or indeterminate LRRK2 status. FIG. 1C. Kaplan-Meier overall survival (OS) stratified by LRRK2 mutation status. Patients with tumors harboring a LRRK2 mutation (N=17) display an OS inferior to patients relative to the BRCA-TCGA cohort, including cases with no LRRK2 mutations or indeterminate LRRK2 status (N=1,079), with 3-year OS of 31% (95% confidence interval [CI]: 0.9/0-74%) versus 84% (95% CI: 79%-87%), respectively. Stars (*) represents extreme outliers, as defined as three times the interquartile range. Of note, breast cancer specific survival data is not available in the BRCA-TCGA cohort.

Figure 2:
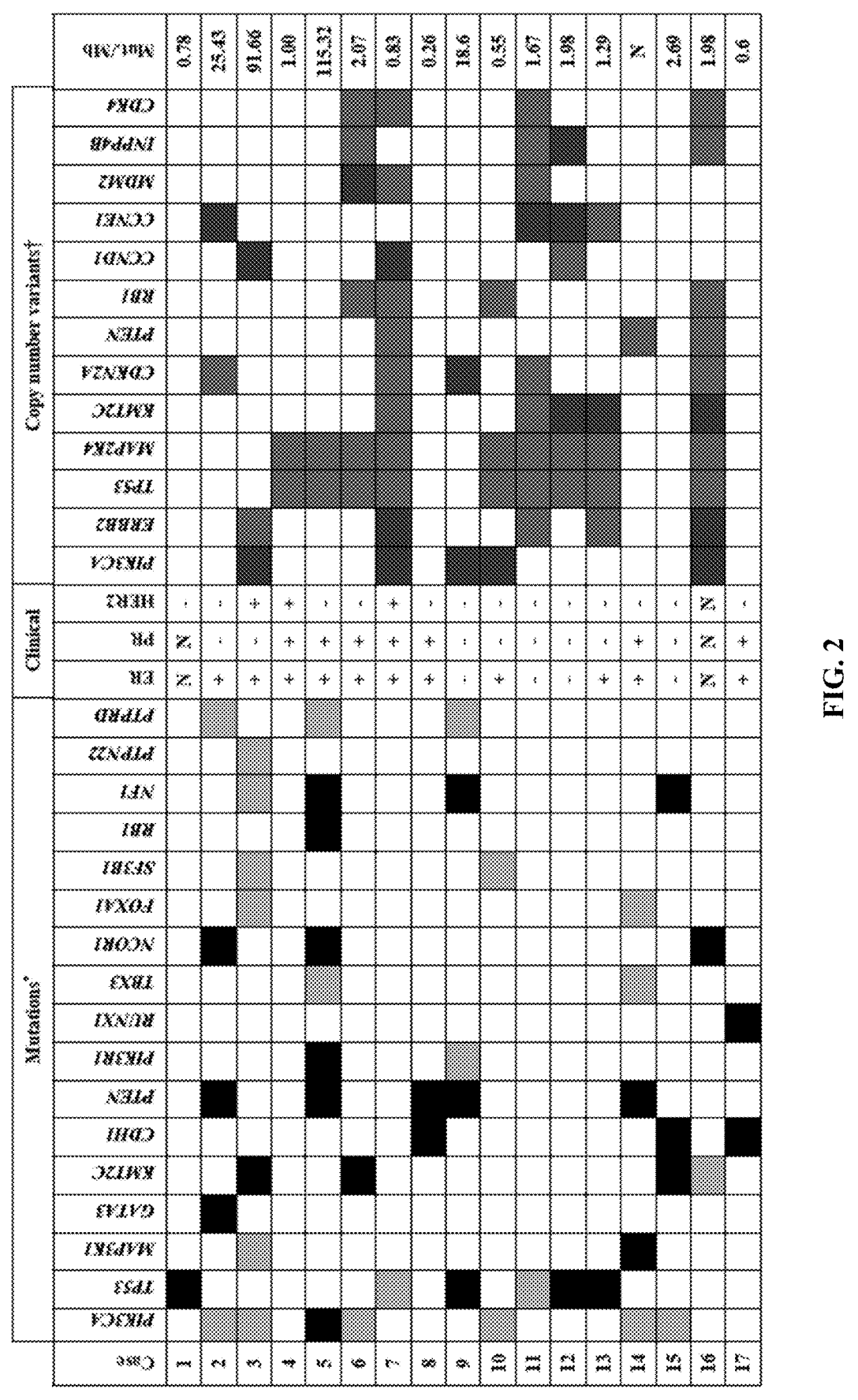

FIG. 2 is a graph showing the genomic landscape of LRRK2 carcinomas in accordance with one embodiment of the present disclosure. In the Mutation columns (*), non-synonymous missense changes are represented by grey boxes and stop-gain mutations (i.e. nonsense, frameshift and splice-site) are in black. In the Copy Number Variants columns (†), copy number gains are represented by dark gray boxes and losses are in light gray boxes. Abbreviations: Not available, N; mutations, Mut.

DETAILED DESCRIPTION

Figures 1A, 1B, 1C:
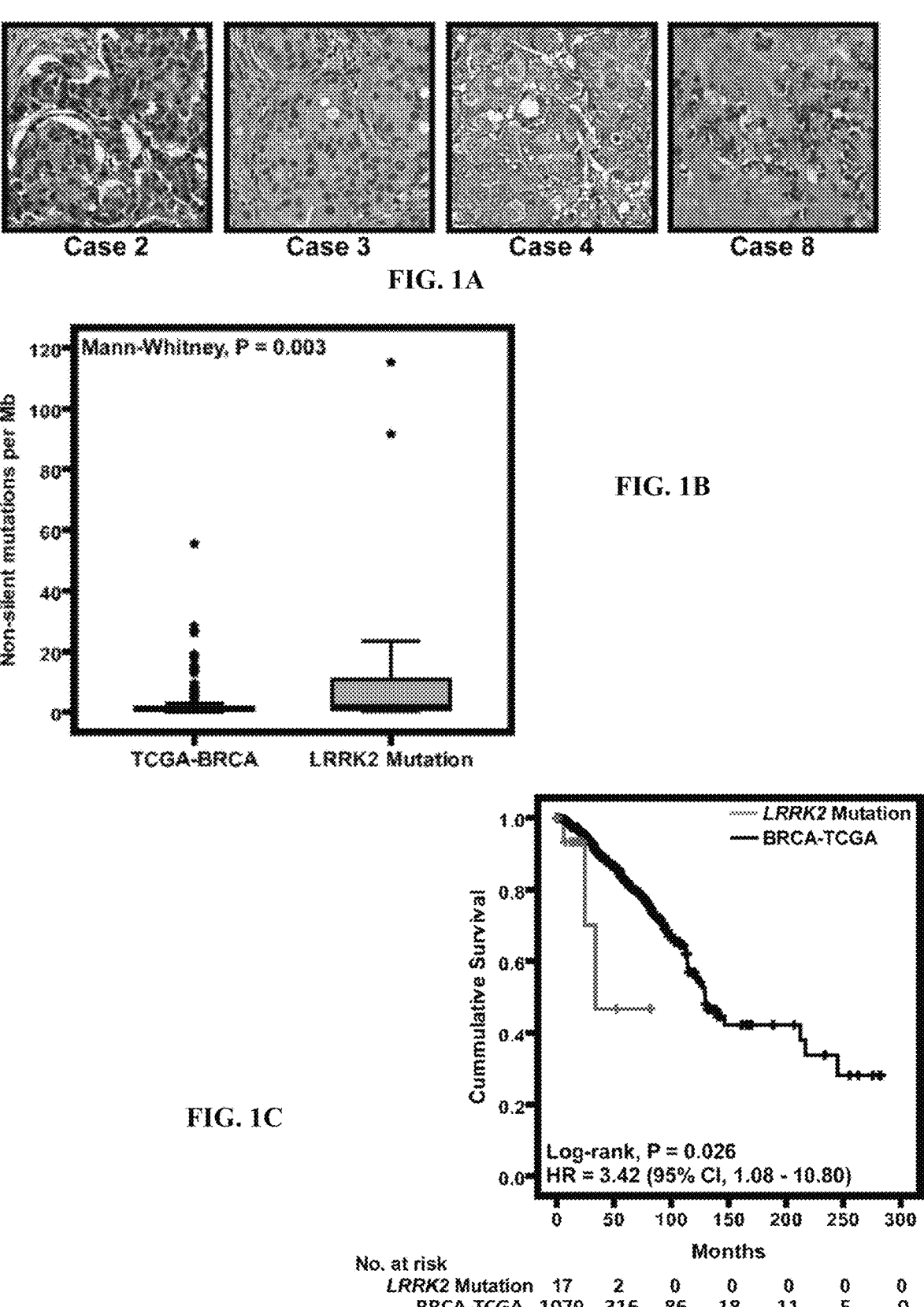
FIGS. 1A-1C are images and graphs showing the clinicopathologic features of LRRK2-mutated invasive mammary carcinomas in accordance with one embodiment of the present disclosure.

This disclosure incorporates by reference for all purposes the entire content of Edgardo R. Parrilla et al., "Somatic Mutations in LRRK2 Identify a Subset of Invasive Mammary Carcinomas Associated with High Mutation Burden", The American Journal of Pathology, Vol. 190, No. 12, December 2020, doi.org/10.1016/j.ajpath.2020.08.010.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used throughout, by "subject" is meant an individual. The term "subject" and "patient" are used interchangeably herein and refer to both human and nonhuman animals. The subject can be an adult subject or a pediatric subject. Adult subjects include subjects older than eighteen years of age. Pediatric subjects include subjects ranging in age from birth to eighteen years of age. Preferably, the subject is an animal, for example, a mammal such as a primate, and, more preferably, a human. Non-human primates are subjects as well. The term subject includes cats, dogs, reptiles, amphibians, livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein. The methods and compositions disclosed herein can be used on a sample either in vitro (for example, on isolated cells or tissues) or in vivo in a subject (i.e. living organism, such as a patient).

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a biopsy (such as a tumor biopsy). A biological sample may be obtained directly from a subject (e.g., by blood or tissue sampling) or from a third party (e.g., received from an intermediary, such as a healthcare provider or lab technician).

As used throughout, the term "gene" refers to a nucleic acid, DNA or RNA, involved in producing or encoding a polypeptide. It may include non-coding regions preceding and following the coding region (leader and trailer) as well as intervening sequences (introns) between individual coding segments (exons). As used throughout, the term "nucleic acid" or "nucleotide" refers to deoxyribonucleic acids (DNA) or ribonucleic acids (RNA) and polymers thereof in either single- or double-stranded form. It is understood that when a DNA sequence is described, its corresponding RNA is also described, wherein thymidine is represented as uridine. Unless otherwise indicated, a particular nucleic acid sequence also implicitly encompasses modified variants thereof, alleles, orthologs, SNPs, and complementary sequences as well as the sequence explicitly indicated.

As used herein, the term polynucleotide or nucleic acid includes nucleotide polymers of any number. The term polynucleotide can, for example, have less than about 200 nucleotides. However, other polynucleotides can have more than 200 nucleotides. Probes and primers are polynucleotides. Primers can, for example, have between 5 and 100 nucleotides, or have about 15 to 100 nucleotides. Probes can have the same or longer lengths. For example, probes can have about 16 nucleotides to about 10,000 nucleotides. The exact length of a particular polynucleotide depends on many factors, which in turn depend on its ultimate function or use. Some factors affecting the length of a polynucleotide are, for example, the sequence of the polynucleotide, the assay conditions in terms of such variables as salt concentrations and temperatures used during the assay, and whether or not the polynucleotide is modified at the 5' terminus to include additional bases for the purposes of modifying the mass: charge ratio of the polynucleotide, or providing a tag capture sequence which may be used to geographically separate a polynucleotide to a specific hybridization location on a DNA chip, for example.

The term "identity" or "substantial identity", as used in the context of a polynucleotide sequence described herein, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, about 20 to 50, about 20 to 100, about 50 to about 200 or about 100 to about 150, in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10-5, and most preferably less than about 10-20.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e. living organism, such as a patient).

As used herein, the term "administering" an agent, such as a therapeutic entity to an animal or cell, is intended to refer to dispensing, delivering or applying the substance to the intended target. In terms of the therapeutic agent, the term "administering" is intended to refer to contacting or dispensing, delivering or applying the therapeutic agent to a subject by any suitable route for delivery of the therapeutic agent to the desired location in the animal, including delivery by either the parenteral or oral route, intramuscular injection, subcutaneous/intradermal injection, intravenous injection, intrathecal administration, buccal administration, transdermal delivery and administration by the intranasal or respiratory tract route.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises breast cancer. In other embodiments, the cancer comprises metastatic breast cancer.

Unless otherwise defined, all technical terms used herein have the same meaning as commonly understood by one of ordinary skill in the art to which this disclosure belongs.

Methods

This disclosure provides a method of determining whether a cancer in a subject is responsive to an immune checkpoint therapy and the method comprises determining the presence or absence of one or more LRRK2 mutations disclosed herein in the subject. If said LRRK2 mutations are present, the subject is determined to be likely to respond to the immune checkpoint therapy. Also provided herein is a method of treating a subject who has been determined to be likely to respond to the immune checkpoint therapy as above by administering the immune checkpoint therapy.

Accordingly, one aspect of the present disclosure provides a method of determining whether a cancer in a subject is responsive to immune checkpoint inhibitor therapy and treating the subject if said determination is made, the method comprising, consisting of, or consisting essentially of: (a) obtaining a biological sample from the subject; (b) determining the presence or absence of at least one LRRK2 mutation as provided herein; and (c) administering to the subject an immune checkpoint therapy if at least one LRRK2 mutation as provided herein is present.

In another aspect, provided is a method of treating a subject with cancer, the method comprising, consisting of, or consisting essentially of, selecting a subject that has at least one LRRK2 mutation as provided in this disclosure and treating the subject by administering an immune checkpoint therapy to the subject.

In some embodiments, the LRRK2 mutations of the provided methods comprise at least one mutation as set forth in Table 1.

In some embodiments, the cancer comprises breast cancer.

In another embodiment, the method further provides administering one or more additional therapies. In some embodiments, the additional therapy is selected from the group consisting of chemotherapy, radiation, surgery, and combinations thereof.

In one embodiment, the at least one additional therapy is administered prior the immune checkpoint therapy. In another embodiment, the at least one additional therapy is administered concurrently with the immune checkpoint therapy. In yet another embodiment, the at least one additional therapy is administered after the immune checkpoint therapy.

In other embodiments, LRRK2 may serve as a drug target for breast (and potentially) other cancers.

Another aspect of the present disclosure provides all that is described and illustrated herein.

LRRK2

Figure 5:
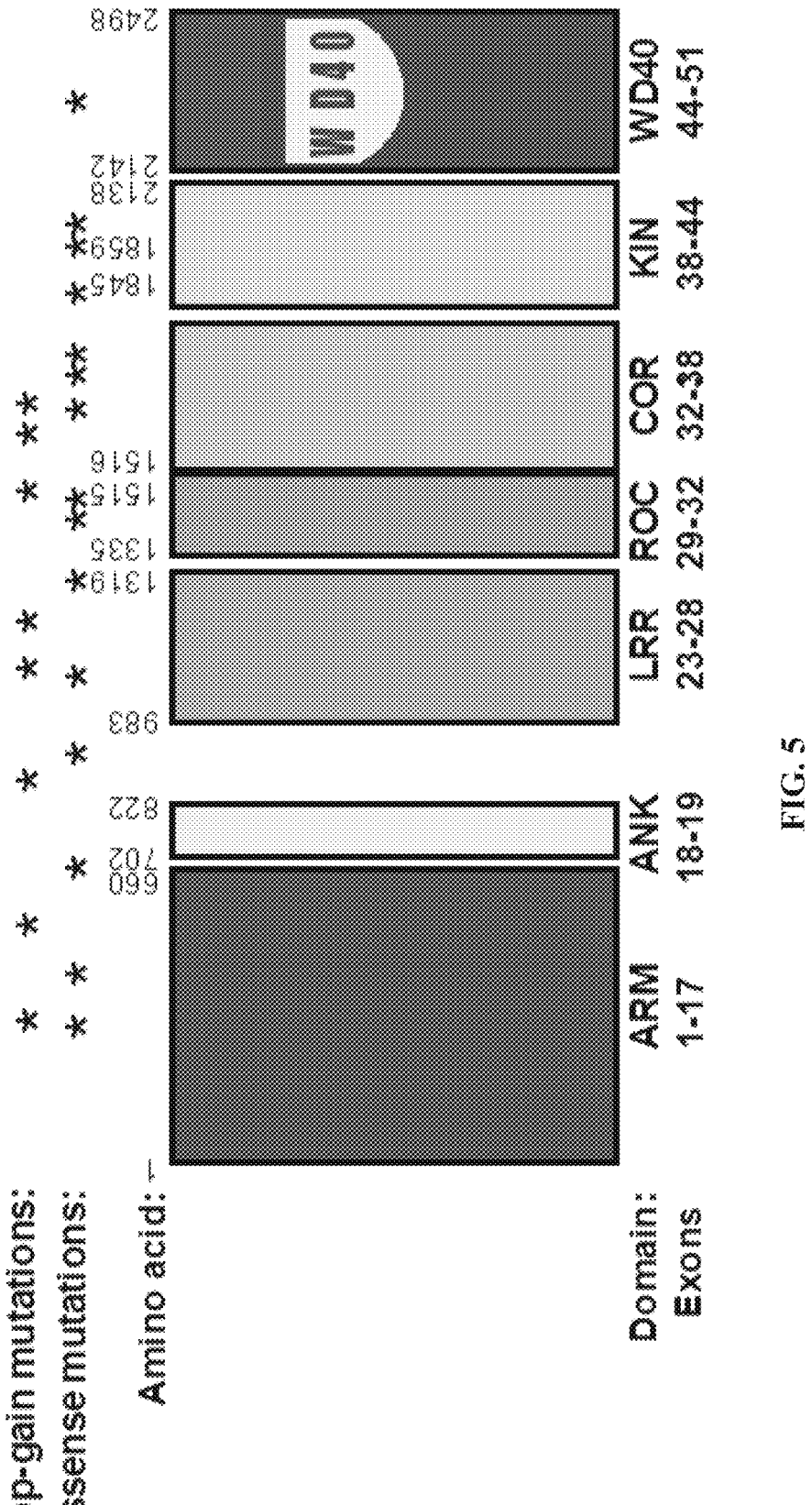
FIG. 5 is a graph showing the distribution of LRRK2 mutations in various domains of the LRRK proteins in accordance with various embodiments of the present disclosure.

LRRK2 is a protein kinase that belongs to the LRRK/ROCO class of protein kinases. As illustrated in FIG. 5, LRRK2 possesses an Armadillo (ARM) domain (spanning exons 1-17), an ANK domain (spanning exons 18-19), an LRR domain (spanning exons 23-28), an ROC domain (exons 29-32), a COR domain (exons 32-38), a Kinase (KIN) domain (spanning exons 38-44), and a WD40 domain (spanning exons 44-51). Various domains of LRRK2 have been characterized in Myasnikov et al., Cell, Vol. 184, Issue 13, 3519-3527 (2021), available at: doi.org/10.1016/j.cell.2021.05.004, the entire content of which is herein incorporated by reference for all purposes. The enzymatic core of the LRRK2 protein is composed of a Ras of complex GTPase domain in tandem with a C-terminal of Roc domain and a kinase domain, which localizes to the cytoplasm and mitochondrial membrane. The wild type human LRRK2 protein has the amino acid sequence set forth in SEQ ID NO:1 and the coding sequence is SEQ ID NO: 2.

LRRK2 Mutation and Pathogenesis

As used herein, the term "LRRK2 mutation" refers to a mutation in the genomic sequence of the human LRRK2 gene that results in a mutant LRRK2 protein having one or more amino acid mutations as compared to SEQ ID NO: 1. Mutations that are associated with disease are referred to as pathogenic mutations. In some embodiments, these LRRK2 pathogenic mutations are clustered among the three domains that form the enzymatic core: the LRRs motif, the Ras-like GTPase domain (ROC) domain, and the COR domain. Some of these mutations have already been reported, a few of which have been shown to cause PD. These include the p.N1437H, p.R1441C/G/H, p.Y1699C, p.S1761R, p.G2019S, p.I2012T, and p.I2020T mutations. See, Coro Paisan-Ruiz et al., J. Parkinsons Dis. 2013; 3(2): 85-103, the entire content of which (including FIG. 1) is herein incorporated by reference. Inventors' own study showed that a large fraction of the mutations in LRRK2 that have been identified were stop-gain, inactivating mutations (41% of cases). Missense variants commonly targeted the Ras of complex, C-terminal of Roc, and kinase domains (Table 1). A single case was characterized by the PD-associated LRRK2 p.G2385R mutation. See Edgardo R. Parrilla et al., "Somatic Mutations in LRRK2 Identify a Subset of Invasive Mammary Carcinomas Associated with High Mutation Burden", The American Journal of Pathology, December 2020, Vol. 190, No. 12, pp. 2478-2482, doi: 10.1016/j.ajpath.2020.08.010 (e-published Sep. 12, 2020).

In some instances, the LRRK2 mutation is a missense mutation. As used herein, "a missense variant" refers to an LRRK2 variant protein that is has a missense mutation in which a single base pair change causes the substitution of a different amino acid in the resulting protein. This amino acid substitution may have no effect, or it may render the protein nonfunctional.

In some instances, the LRRK2 mutation is a stop-gain mutation. As used herein, the term "stop-gain" refers to a mutation that results in a premature termination codon (a stop was gained), which signals the end of translation from the DNA sequence encoding the protein. This interruption causes the protein to be abnormally shortened. The number of amino acids lost mediates the impact on the protein's functionality and whether it will function whatsoever.

In some instances, the LRRK2 mutation is a nonsense mutation. A nonsense mutation is a point mutation in a DNA sequence encoding a protein that results in a premature stop codon, or a nonsense codon in the transcribed mRNA, and in a truncated, incomplete, and usually nonfunctional protein product. The functional effect of a nonsense mutation depends on the location of the stop codon within the coding DNA.

In some instances, the LRRK2 mutation is a frameshift mutation. A frameshift mutation is a type of mutation involving the insertion or deletion of a nucleotide in which the number of deleted base pairs is not divisible by three. "Divisible by three" is important because the cell reads a gene in groups of three bases. Each group of three bases corresponds to one of 20 different amino acids used to build a protein. If a mutation disrupts this reading frame, then the entire DNA sequence following the mutation will be read incorrectly.

LRRK2 mutations from patients with wildtype/polymorphic variant LRRK2 sequences and patients with variants with insufficient evidence for pathogenicity are listed in Table 2. Thus, in some embodiments, the LRRK mutations present in cancer patients who can benefit from the methods and compositions disclosed herein do not include any one of the mutations in Table 2.

Detecting LRRK2 Mutations

As used herein, LRRK2 protein refers to both wild type LRRK2 and also LRRK2 variants (i.e. LRRK2 mutants). In some embodiments, a LRRK2 variant protein comprises one or more LRRK2 mutations disclosed herein. In some embodiments, the subject who would benefit from the immune checkpoint therapy according to the methods described herein expresses a LRRK2 variant protein that has decreased kinase activity (including variants that have a loss of kinase activity) as compared to the wild type LRRK2 protein. Non-limiting examples of a LRRK2 variant protein that has decreased kinase activity include those disclosed in Table 1.

In some embodiments, a subject who can benefit from the immune checkpoint therapy according to the methods described herein expresses a LRRK2 variant having at least 60%, 65%, 70%, 75%, 80%, 85%, 90%, 95%, and/or 99% identity to SEQ ID NO: 1, provided that the LRRK2 variant has decreased kinase activity as compared to the wild type LRRK2. In some embodiments, the LRRK2 variants has less than twenty, less than fifteen, less than ten, less than nine amino acid mutations (substitutions, deletions, or insertions) relative to SEQ ID NO: 1, provided that the LRRK2 variant has decreased kinase activity as compared to the wild type LRRK2.

As used herein, having decreased kinase activity refers to the kinase activity of the LRRK2 variant being less than 90%, less than 80%, less than 70%, less than 60%, less than 50%, less than 40%, less than 30%, less than 25%, less than 20%, or less than 10% of the kinase activity of the wild type LRRK2 protein as determined using the same assay. The kinase activity of the variant can be assessed by analyzing phosphorylation of a substrate of the kinase. Exemplary substrates of the LRRK2 include moesin, MBP, and LRRKtide as disclosed in Jaleel, et al., Biochem J. 2007 Jul. 15, 405(Pt 2): 307-317. Methods of analyzing LRRK2 kinase activity are well known and also disclosed, for example, in Jaleel, et al., Biochem J. 2007 Jul. 15, 405(Pt 2): 307-317. Mutations in LRRK2 can be detected using methods suitable for detecting mutations, for example, the mutations in Table 1, in the LRRK2 gene that encodes the LRRK2 variants. Useful techniques include, without limitation, assays such as polymerase chain reaction (PCR) based analysis assays, sequence analysis assays, electrophoretic analysis assays, restriction length polymorphism analysis assays, hybridization analysis assays, allele-specific hybridization, oligonucleotide ligation allele-specific elongation/ligation, allele-specific amplification, single-base extension, molecular inversion probe, invasive cleavage, selective termination, restriction length polymorphism, sequencing, single strand conformation polymorphism (SSCP), single strand chain polymorphism, mismatch-cleaving, and denaturing gradient gel electrophoresis, all of which can be used alone or in combination.

Any of a variety of different primers can be used to amplify an individual's nucleic acid by PCR in order to determine the presence or absence of a mutation in LRRK2 disclosure. As understood by one skilled in the art, primers for PCR analysis can be designed based on the sequence flanking the target sequence in the LRRK2 gene. As a non-limiting example, a primer can contain from about 15 to about 30 nucleotides of a sequence upstream or downstream of the the target sequence in the gene of interest. Such primers generally are designed to have sufficient guanine and cytosine content to attain a sufficiently high melting temperature to allow for a stable annealing step in the amplification reaction. Several computer programs, such as Primer Select, are available to aid in the design of PCR primers.

Sequence analysis can also be useful for determining the presence or absence of a particular variant or haplotype in the gene or locus of interest. As is known by those skilled in the art, a variant allele of interest can be detected by sequence analysis using the appropriate primers, which are designed based on the sequence flanking the polymorphic site of interest in the gene or locus of interest. For example, a variant allele in a gene or locus of interest can be detected by sequence analysis using primers designed by one of skill in the art. Additional or alternative sequence primers can contain from about 15 to about 30 nucleotides of a sequence that corresponds to a sequence about 40 to about 400 base pairs upstream or downstream of the polymorphic site of interest in the gene or locus of interest. Such primers are generally designed to have sufficient guanine and cytosine content to attain a high melting temperature which allows for a stable annealing step in the sequencing reaction.

Treatment

Also disclosed herein are methods of treating a cancer having the LRRK2 mutations as disclosed herein by administering a subject in need a therapeutically effective amount of an immune checkpoint therapy.

As used herein, the term "immune checkpoint therapy" refers to a therapy that uses an immune checkpoint inhibitor to inhibit or down-regulate at least partially the function of an inhibitory immune checkpoint. Immune checkpoint therapy can be used to reduce and/or stop the growth of a cancer cell.

In some instances, immune checkpoint inhibitors bind to T-cell inhibitory receptors including but not limited to PD-1 (programmed death-1, also referred to as CD279), TIM3 (T-cell immunoglobulin and mucin-domain containing-3 3; also known as HAVcr2), BTLA (B and T lymphocyte attenuator; also known as CD272), the VISTA (B7-H5) receptor, LAG3 (lymphocyte activation gene 3; also known as CD233) and CTLA4 (cytotoxic T-lymphocyte associated antigen 4; also known as CD152). In some instances, immune checkpoint inhibitors bind to the ligand of T-cell inhibitory receptors including but not limited to PD-L1 (programmed death-1 ligand, also referred to as CD274 and D7-H1).

Exemplary immune checkpoint inhibitors include but are not limited to PD-1/PD-L1 pathway inhibitors (also referred to as PD-1 pathway inhibitors), TIM3 pathway inhibitors, and anti-cytotoxic T-lymphocyte antigen 4 (CTLA4) pathway inhibitors.

In one embodiment, the immune checkpoint inhibitor inhibits the binding of PD-1 to PD-L1 and/or PD-L2 (referred to as a "PD-1 pathway inhibitor" or a "PD-1/PD-L1 pathway inhibitor"). Such inhibitors include PD-1 inhibitors and PD-L1 inhibitors, which bind to PD-1 and PD-L1, respectively. Such inhibitors act to inhibit the association of PD-L1 with its receptor PD-1. The interaction of these cell surface proteins is involved in the suppression of the immune system and occurs following infection to limit the killing of bystander host cells and also prevents autoimmune disease. Examples of commercially available PD-1 pathway inhibitors useful as supplementary agents in the treatment of neoplastic disease include antibodies that interfere with the binding of PD-1 to PD-L1 and/or PD-L2. Such antibodies include but are not limited to nivolumab (Opdivo®, BMS- 936558, MDX1106, commercially available from Bristol Myers Squibb, Princeton NJ), pembrolizumab (Keytruda®MK-3475, lambrolizumab, commercially available from Merck and Company, Kenilworth NJ), and atezolizumab (Tecentriq®, Genentech/Roche, South San Francisco CA), Libtayo™ (Regeneron Pharmaceuticals, Inc., and Sanofi-Aventis), avelumab (Bacencio™, EMD Serono Inc.), and durvalumab (Imfinzi™, Astra-Zeneca). Additional PD-1/PD-L1 pathway inhibitors antibodies are in clinical development and include but not limited to durvalumab (MEDI4736, Medimmune/AstraZeneca), pidilizumab (CT-011, CureTech), PDR001 (Novartis), BMS-936559 (MDX1105, BristolMyers Squibb), avelumab (MSB0010718C, Merck Serono/Pfizer), and SHR-1210 (Incyte). Other exemplary PD-1/PD-L1 pathway inhibitors include AMP-224, a PD-L2 IgG2a fusion protein, and AMP-514, a PDL2 fusion protein, aptamers (Wang, et al. (2018) 145:125-130), peptide PD-1 pathway inhibitors (U.S. Pat. Nos. 9,422,339; 8,907,053), and small molecule PD-1 pathway inhibitors (see, WO2016142833A1, WO 2015/034820 A1, EP3041822 B1, WO2015034820 A1; U.S. Pat. No. 7,488,802).

In one embodiment, the immune checkpoint inhibitor inhibits the binding of CTLA4 to CD80 and/or CD86 (referred to as a "CTLA4 pathway inhibitor" or a "CTLA4 inhibitor"). CTLA4 functions as an immune checkpoint and downregulates immune responses. Examples of CTLA4 pathway inhibitors are well known in the art and include, e.g., ipilimumab (Yervoy™) (see, e.g., U.S. Pat. Nos. 6,682, 736; 6,984,720; 7,605,238).

In one embodiment, the immune checkpoint inhibitor inhibits the ability TIM3 to binding to TIM3-activating ligands (referred to as a "TIM3 pathway inhibitor" or a "TIM3 inhibitor"). TIM3 is an immune checkpoint and, together with other inhibitory receptors like PD-1 and LAC3, mediate CD8+ T-cell exhaustion (e.g., in chronic viral infections and cancer). Examples of TIM3 pathway inhibitors are known in the art and include representative non-limiting examples as described in PCT International Patent Publication No. WO 2016/144803; United States Patent Publication No. US 20160257749 A1; and U.S. Pat. Nos. 9,631,026; 8,841,418; 9,605,070; and 8,552,156.

As used throughout this disclosure, "effective amount," or "therapeutically effective amount," refers to an amount of a therapeutic agent (e.g., an immune checkpoint therapy or additional therapy as discussed below) sufficient to effect beneficial or desirable biological and/or clinical results. The effective amount of any of the therapeutic agents described herein (e.g., the immune checkpoint modulator) can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Other factors that influence dosage can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

As used herein, administer or administration refers to the act of introducing, injecting or otherwise physically delivering a substance as it exists outside the body into a subject, such as by mucosal, intradermal, intravenous, intratumoral, intramuscular, intrathecal, intracranial, intrarectal, oral, subcutaneous delivery and/or any other method of physical delivery described herein or known in the art.

Any of the therapeutic agents described herein, including immune checkpoint therapies and additional therapies as described below, can be administered in a number of ways depending on whether local or systemic treatment is desired, and on the area to be treated. The compositions are administered via any of several routes of administration, including orally, parenterally, intrathecally, intracranially, intramucosally, intravenously, intraperitoneally, intraventricularly, intramuscularly, subcutaneously, intracavity or transdermally. Administration can be achieved by, e.g., topical administration, local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; and European Patent Nos. EP488401 and EP 430539. In some methods, the therapeutic agent can be delivered to the subject by way of an implantable device based on, e.g., diffusive, erodible, or convective systems, osmotic pumps, biodegradable implants, electrodiffusion systems, electroosmosis systems, vapor pressure pumps, electrolytic pumps, effervescent pumps, piezoelectric pumps, erosion-based systems, or electromechanical systems. Effective doses for any of the administration methods described herein can be extrapolated from dose-response curves derived from in vitro or animal model test systems.

Dosage regimens of any of the therapeutic agents described herein, including immune checkpoint therapies and additional therapies as described below, are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b)

the limitations inherent in the art of compounding such an active compound for the treatment of sensitivity in individuals.

Any of the therapeutic agents described herein, including immune checkpoint therapies and additional therapies as described below, can be formulated as a pharmaceutical composition. In some embodiments, the pharmaceutical composition can further comprise a carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, a pharmaceutical composition comprising a therapeutic agent described herein, including immune checkpoint therapies and additional therapies as described below, can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

Additional Therapies (Chemotherapy, Radiation, Surgery)

In some embodiments, the present methods of treating cancer in subjects having the LRRK2 mutations described in this disclosure involve administering one or more immune checkpoint modulators described above in combination with other means of anti-cancer therapy, such as surgery, and/or radiation.

By "combination therapy" or "in combination with", it is not intended to imply that the therapeutic agents must be administered at the same time and/or formulated for delivery together, although these methods of delivery are within the scope described herein. The immune checkpoint modulator and the additional therapy can be administered following the same or different dosing regimen. In some embodiments, the immune checkpoint modulator and the additional therapy are administered sequentially in any order during the entire or portions of the treatment period. In some embodiments, the immune checkpoint modulator and the additional anti-cancer therapy is administered simultaneously or approximately simultaneously (e.g., within about 1, 5, 10, 15, 20, or 30 minutes of each other).

Chemotherapeutic agents suitable for use in combination with the immune checkpoint modulator of the invention include agents that have the property of killing cancer cells or inhibiting cancer cell growth. As compared to targeted therapies as described above, chemotherapies function in a non-specific manner, for example, inhibiting the process of cell division known as mitosis, and generally excludes agents that more selectively block extracellular growth signals (i.e. blockers of signal transduction). These agents include, but are not limited to, anti-microtubule agents (e.g., taxanes and *vinca* alkaloids), topoisomerase inhibitors and antimetabolites (e.g., nucleoside analogs acting as such, for example, Gemcitabine), mitotic inhibitors, alkylating agents, antimetabolites, anti-tumor antibiotics, mitotic inhibitors, anthracyclines, intercalating agents, agents capable of interfering with a signal transduction pathway, agents that promote apoptosis, proteosome inhibitors, and alike.

Alkylating agents are most active in the resting phase of the cell. These types of drugs are cell-cycle non-specific. Exemplary alkylating agents that can be used in combination with the immune checkpoint modulator to treat the cancer disclosed herein include, without limitation, nitrogen mustards, ethylenimine derivatives, alkyl sulfonates, nitrosoureas and triazenes: uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Antitumor antibiotics are chemotherapeutic agents obtained from natural products produced by species of the soil fungus *Streptomyces*. These drugs act during multiple phases of the cell cycle and are considered cell-cycle specific. There are several types of antitumor antibiotics, including but are not limited to Anthracyclines (e.g., Doxorubicin, Daunorubicin, Epirubicin, Mitoxantrone, and Idarubicin), Chromomycins (e.g., Dactinomycin and Plicamycin), Mitomycin and Bleomycin.

Antimetabolites are types of chemotherapy treatments that are cell-cycle specific. When the cells incorporate these antimetabolite substances into the cellular metabolism, they are unable to divide. This class of chemotherapy agents include folic acid antagonists such as Methotrexate; pyrimidine antagonists such as 5-Fluorouracil, Foxuridine, Cytarabine, Capecitabine, and Gemcitabine; purine antagonists such as 6-Mercaptopurine and 6-Thioguanine; Adenosine deaminase inhibitors such as Cladribine, Fludarabine, Nelarabine and Pentostatin.

Exemplary anthracyclines that can be used in combination with the immune checkpoint modulator to treat a cancer disclosed herein include, e.g., doxorubicin (Adriamycin® and Rubex®); Bleomycin (Lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence®); Idarubicin (Idamycin®, Idamycin PFS®); Mitomycin C (Mutamycin®); Geldanamycin; Herbimycin; Ravidomycin; and Desacetylravidomycin.

Antimicrotubule agents include *vinca* alkaloids and taxanes. Exemplary *vinca* alkaloids that can be used in combination with the immune checkpoint modulator to treat a cancer disclosed herein include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary taxanes that can be used in combination with the immune checkpoint modulator to treat the cancer disclosed herein include, but are not limited to, paclitaxel and docetaxel. Non-limiting examples of paclitaxel agents include nanoparticle albumin-bound paclitaxel (ABRAXANE, marketed by Abraxis Bioscience), docosahexaenoic acid bound-paclitaxel (DHA-paclitaxel, Taxoprexin®, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., Bioorganic & Medicinal Chemistry Letters (2007) 17:617-620).

Exemplary proteosome inhibitors that can be used in combination with the immune checkpoint modulator to treat a cancer disclosed herein include, but are not limited to, Bortezomib (Velcade®); Carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(-2R)-2-methyl-2-oxiranyl]-2-oxo-1-(phenylmethyl)ethyl]-L-serinamide (ONX-0912).

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, doxorubicin, paclitaxel, docetaxel, gemcitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, gemcitabine, Irinotecan, albumin-bound paclitaxel, Oxaliplatin, Capecitabine, Cisplatin, docetaxel, irinotecan liposome, and etoposide, and combinations thereof.

In certain embodiments, the chemotherapeutic agent is administered at a dose and a schedule that may be guided by doses and schedules approved by the U.S. Food and Drug Administration (FDA) or other regulatory body, subject to empirical optimization.

In still further embodiments, more than one chemotherapeutic agent may be administered simultaneously, or sequentially in any order during the entire or portions of the treatment period. The two agents may be administered following the same or different dosing regimens.

Radiotherapy requires maximized exposure of the affected tissues while sparing normal surrounding tissues. Interstitial therapy, where needles containing a radioactive source are embedded in the tumor, has become a valuable new approach. In this way, large doses of radiation can be delivered locally while sparing the surrounding normal structures. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures.

In some embodiments, the immune checkpoint therapy disclosed herein can be administered in combination with surgery to remove cancerous tissue. For example, in the context of breast cancer, the surgery may comprise a lumpectomy, a quadrantectomy, a partial mastectomy, a segmental mastectomy, or a full mastectomy. In some instances, the surgery may also comprise removal of one or more lymph nodes. In some instances, the surgery may comprise removal of cancerous tissue at a metastatic site.

Pharmaceutical Compositions

In performance of these methods, the present disclosure further provides for pharmaceutical compositions comprising effective amounts of the foregoing agents/compounds (e.g., ATM kinase inhibitor(s)), separately or in combination with another therapeutic agent, in a suitable pharmaceutical carrier. The foregoing agents/compounds may be administered orally, intravenously, subcutaneously, intramuscularly, intranasally, intrathecally, or by other methods, several of which are known in the art, as would be appropriate for the chemical properties of the compound. It will be apparent to a person of ordinary skill in the art to determine the appropriate method of delivery of the foregoing agents/compounds.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenylsubstituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Any of the methods provided herein can also be performed by use of kits that are described herein. Provided herein is a kit comprising agents for detection of the mutations in LRRK2 gene. Such agents may include primers for amplifying DNA, sequencing primers and enzymes that can be used in the PCR reactions or sequencing reactions.

In some embodiments, the kit further comprises pharmaceutical compositions comprising one or more checkpoint modulators as disclosed above.

In some embodiments the kit further comprises instructions on how to use the kit to detect mutations in LRRK2 gene and/or administer the ATM inhibitors.

The kits can include components for isolating and/or detecting DNA in essentially any sample (e.g., urine, blood, etc.), and a wide variety of reagents and methods are, in view of this specification, known in the art. Hence, the kits can include vials, swabs, needles, syringes, labels, pens, pencils, or combinations thereof.

In some embodiments, commercially available components can also be included in the kits. For example, the kit can include components from QIAGEN, which manufactures a number of components for DNA isolation.

The kits can also include any of the following components: materials for obtaining a sample, enzymes, and buffers. One of skill in the art would, in view of this specification, readily understand many combinations of components that a kit of the invention may comprise.

Exemplary Embodiments

This disclosure provides the following nonlimiting exemplary embodiments.

Embodiment 1. A method of determining whether a cancer in a subject is responsive to an immune checkpoint therapy and treating the subject if said determination is made, the method comprising: (a) obtaining a biological sample from the subject; (b) determining the presence or absence of at least one LRRK2 mutation as provided herein; and (c) administering to the subject an immune checkpoint therapy (if at least one LRRK2 mutation as provided herein is present.

Embodiment 2. The method according to embodiment 1 in which the LRRK2 mutations comprise at least one mutation as provided in Table 1.

Embodiment 3. The method according to any of the preceding embodiments in which the cancer comprises breast cancer.

Embodiment 4. The method as in any of the preceding embodiments in which the method further provides administering one or more additional therapies.

Embodiment 5. The method according to embodiment 4 in which the additional therapy is selected from the group consisting of chemotherapy, radiation, surgery, and combinations thereof.

Embodiment 6. The method as in any of embodiments 4 or 5 in which the at least one additional therapy is administered prior the immune checkpoint therapy.

Embodiment 7. The method as in any of embodiments 4 or 5 in which the at least one additional therapy is administered concurrently with the immune checkpoint therapy.

Embodiment 8. The method as in any of embodiments 4 or 5 in which the at least one additional therapy is administered after the immune checkpoint therapy.

Embodiment 9. A method of determining whether a cancer in a subject is responsive to immune checkpoint therapy and treating the subject if said determination is made, the method comprising: (a) obtaining a biological sample from the subject; (b) determining the presence or absence of one or more LRRK2 mutations; and (c) administering to the subject an immune checkpoint therapy if one or more LRRK2 mutations as provided herein is present.

Embodiment 10. A method of treating a subject with cancer, the method comprising, consisting of, or consisting essentially of, selecting a subject that has at least one LRRK2 mutation as provided in this disclosure and treating the subject by administering a therapeutically effective amount of an immune checkpoint therapy to the subject.

Embodiment 11. The method of embodiment 9 or 10 in which the the immune checkpoint therapy is administering a therapeutically effective amount of an immune checkpoint inhibitor.

Embodiment 12. The method of of any one of embodiments 9-11, wherein the one or more LRRK2 mutations results in reduced kinase activity of the LRRK2 protein, and wherein the one or more LRRK2 mutations is located in one or more domains of the LRRK2 protein: the Armadillo domain, the inter-domain, the leucine-rich repeat ROC domain, the kinase domain, or the WD40 domain.

Embodiment 13. The method of any one of embodiments 9-12, wherein the one or more LRRK2 mutations are one or more of a missense mutation, a frameshift mutation, or a nonsense mutation.

Embodiment 14. The method of any one of embodiments 9-13, wherein the one or more LRRK2 mutations comprise one or more mutations as provided in Table 1.

Embodiment 15. The method of embodiment 14, wherein the one or more LRRK2 mutations do not comprise any of the mutations as provided in Table 2.

Embodiment 16. The method of embodiment 14, wherein the one or more LRRK2 mutations do not comprise any of the mutations as provided in Table 3.

Embodiment 17. The method of any one of embodiments 9-16, wherein the one or more LRRK2 mutations do not comprise any of mutations p.N1437H, p.R1441C/G/H, p.Y1699C, p.S1761R, p.G2019S, p.I2012T, and p.I2020T.

Embodiment 18. The method according to any of the preceding embodiments wherein the cancer comprises breast cancer.

Embodiment 19. The method of any of the preceding embodiments, wherein the method further provides administering one or more additional therapies to treat the cancer.

Embodiment 20. The method of embodiment 19, wherein the additional therapy is one or more of chemotherapy, radiation, surgery, or combinations thereof.

Embodiment 21. The method of embodiment 19 or 20, wherein the at least one additional therapy is administered prior to the immune checkpoint therapy.

Embodiment 22. The method of any one of embodiments 19-21 wherein the at least one additional therapy is administered concurrently with the immune checkpoint therapy.

Embodiment 23. The method of any one of embodiments 19-21, wherein the at least one additional therapy is administered after the immune checkpoint therapy.

Embodiment 24, The method of any of the preceding embodiments, wherein the immune checkpoint therapy is administering an PD-1 inhibitor or an PD-L1 inhibitor.

Embodiment 25. The method of any of the preceding embodiments, wherein the immune checkpoint therapy is administering a CTLA-4 inhibitor.

Embodiment 26. The method of any of the preceding embodiments, wherein the immune checkpoint therapy is administering a TIM3 inhibitor.

Embodiment 27. A method of treating a subject with cancer, the method comprising, consisting of, or consisting essentially of, selecting a subject that has at least one LRRK2 mutation as provided in this disclosure and treating the subject by administering a therapeutically effective amount of an immune checkpoint therapy to the subject.

Embodiment 28. A kit for treating a subject having cancer, the kit comprising (1) primers for detecting one or more LRRK2 mutations in a biological sample, wherein the one or more LRRK2 mutations result in reduction in kinase activity of LRRK2 as compared to the wild type LRRK2 and (2) instructions for identifying one or more LRRK mutations.

Embodiment 29. The kit of embodiment 28, wherein the one or more LRRK2 mutation results in reduced kinase activity of the LRRK2, and wherein one or more LRRK2 mutations is located in one or more domains of the LRRK2 protein: the Armadillo domain, the inter-domain, the leucine-rich repeat ROC domain, the kinase domain, or the WD40 domain.

Embodiment 30. The kit of embodiment 28 or 29, wherein the one or more mutations are listed in Table 1.

Embodiment 31. The kit of any one of embodiments 28-30, wherein the cancer is breast cancer.

Embodiment 32. Any and all methods, processes, devices, systems, devices, kits, products, materials, compositions and/or uses shown and/or described expressly or by implication in the information provided herewith, including but not limited to features that may be apparent and/or understood by those of skill in the art.

Embodiment 32. All that is described and illustrated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The following Examples are provided by way of illustration and not by way of limitation.

EXAMPLES

Example 1. Somatic Mutations in LRRK2 Identify a Subset of Invasive Mammary Carcinomas Associated with High Mutation Burden A. Materials and Methods Clinical information, simple somatic mutations (SSM), including single nucleotide variants and small insertions/deletions, from whole exome sequencing and copy number information available through the Cancer Genome Atlas Breast Cancer Project (TCGA-BRCA) were downloaded from the Genomic Data Commons (GDC) Data Portal. For an extensive description of the tumor variant annotation workflow performed by the GDC DNA-Seq analysis pipeline (see: docs.gdc.cancer.gov/Data/Bioinformatics Pipelines/DNA_Seq_Variant_Calling_Pipeline/#tumor-only-variant-annotation-workflow (7/10/20)).

The SSM, single nucleotide variants and small insertions/deletions were subjected to the current guidelines by the American College of Medical Genetics. Briefly, LRRK2 nonsense, frameshift, and canonical splice-site sequence variants were considered pathologically significant since all of these types of mutations lead to either a stop codon, truncated, incomplete or typically nonfunctional protein product. The remaining variants were compared to published data or were evaluated using in silico analyses. SIFT, MutationTaster, and PolyPhen were used to evaluate missense variants and only considered pathogenic if consistently predicted deleterious by all three programs (Table 1).

TABLE 1

LRRK2 mutations, predicted protein change, variant type and domain affected from the Cancer Genome Atlas (TCGA)

| Case | Barcode | Coding | Protein | Variant Type | Domain |
|------|---------|--------|---------|--------------|--------|
| 1 | TCGA-E9-A243 | c. 1274T > C | p.L425P | Missense | Armadillo |
| 2 | TCGA-AN-A0AK | c. 1605del | p.K535Nfs*13 | Frameshift | Armadillo |
| 3 | TCGA-AC-A23H | c.2573C > G | p.S858* | Nonsense | Inter-domain |
| 4 | TCGA-C8-A132 | c.2765T > A | L922* | Nonsense | Inter-domain |
| 5 | TCGA-AN-A046 | c.3266A > G | p.N1089S | Missense | Leucine-rich |
| | | c.4469C > T | p.A1490V | Missense | repeat & ROC |
| 6 | TCGA-D8-A1JP | c.3910C > T | p.L1304F | Missense | Leucine-rich repeat |
| 7 | TCGA-D8-A1X5 | c.4334C > T | p.S1445F | Missense | ROC |
| 8 | TCGA-BH-A0E9 | c.4514_4520del | p.I1505Rfs*16 | Frameshift | ROC |
| 9 | TCGA-D8-A1XK | c.4915dup | p.R1639Kfs*13 | Frameshift | COR |
| 10 | TCGA-AN-A0XO | c.5072T > C | p.I1691T | Missense | COR |
| 11 | TCGA-AO-A0J4 | c.5117C > G | p.S1706* | Nonsense | COR |
| 12 | TCGA-AN-A0XU | c.5312G > C | p.R1771T | Missense | COR |
| 13 | TCGA-D8-A1XZ | c.5455G > C | p.G1819R | Missense | COR |
| 14 | TCGA-S3-AAll | c.5861C > T | p.S1954F | Missense | Kinase |
| 15 | TCGA-C8-A3M7 | c.6322G > A | p.E2108K | Missense | Kinase |
| 16 | TCGA-B6-A018 | c.7153G > A | p.G2385R | Missense | WD40 |

(*denotes a stop codon)

Notes: 4514_4520del means a deletion of region between position 4514 and position 4520 (end amino acid residues inclusive); 4915dup means the nucleotide at position 4915 are duplicated; "p.?" refers to that it is unknown whether this mutation will affect the LRRK2 protein sequence.

Those variants that did not meet these strict criteria for pathogenicity and are of unknown significance are included in Table 2. No germline variants were included in the analysis.

TABLE 2

LRRK2 variants excluded from TCGA analysis, predicted protein change.

| Barcode | Coding | Protein | Comment |
|---------|--------|---------|---------|
| TCGA-BH-A1FN | c.2515C > A | p.Leu839Ile | Poorly preserved nucleotide; aliphatic to aliphatic amino acid change; in silico analyses with inconsistent predictions |
| TCGA-EW-A1J5 | c.2609C > G | p. Ser870Cys | Polymorphic nucleotide; poorly preserved amino acid; in silico analyses with inconsistent predictions |
| TCGA-A8-A09G | c.3777 + 135C > G | p.? | Deep intronic variant |
| TCGA-D8-A1XQ | c.4473C > G | p.Thr1491Thr | Synonymous |
| TCGA-A8-A0A7 | c.4671G > A | p. Val1557Val | Synonymous |
| TCGA-AR-A1AR | c.6471T > G | p.A1a2157Ala | Synonymous |
| TCGA-BH-A0HF | c.7390 + 170G > A | p.? | Deep intronic variant |
| TCGA-A8-A09Z | c.7391-58dup | p.? | Deep intronic variant |
| TCGA-B6-A0RI | c.7462 + 63A > C | p.? | Deep intronic variant |

TABLE 2-continued

LRRK2 variants excluded from TCGA analysis, predicted protein change.

| Barcode | Coding | Protein | Comment |
|---------|--------|---------|---------|
| TCGA-AC-A23H | c.7522G > C | p.Glu2508Gln | Poorly preserved nucleotide/amino acid; in silico analyses consistently predict not pathogenic |

Processed, normalized, and segmented data from Affymetrix SNP 6.0 arrays were used to generate masked copy number segment files, and numeric focal-level copy number variation (CNV) values were obtained using GISTIC2 (Genomic Data Commons Copy Number Variation Analysis Pipeline). CNV with values<−0.3 were categorized as "loss" and values>0.3 were categorized as "gain". Non-synonymous mutations rates from 988 of 1,098 cases computed by the Broad Genome Data Analysis Center using MutSigCV (v0.9) were obtained from FireBrowse. The rate of non-synonymous gene mutations was determined by the Broad Genome Data Analysis Center using MutSigCV v.0.9. *Broad Institute TCGA Genome Data Analysis Center (2016): Mutation Analysis (MutSigCVv0.9). Broad Institute of MIT and Harvard. doi:10.7908/C1PK0FH7.

Whole slide images of diagnostic sections were downloaded from the GDC Data Portal and assessed by at least one breast pathologist on ImageScope. Select clinical data, follow-up times and vital status were available for 1,096 of 1,098 patients. Overall survival was defined as date of diagnosis to the date of last clinical follow-up or death. Simple somatic mutations were also downloaded and analyzed from the cBio Cancer Genomics Portal. Statistical analysis included comparisons between the groups using either the Chi-Square, Mann-Whitney (where tests for homoscedasticity failed to demonstrate equal variances), and Mantel-Cox log rank tests.

B. Results

Curated clinical, mutation, and copy number information was available for 1,098 of The Cancer Genome Atlas (TCGA) project-level breast cancer cases. Due to the large size of LRRK2 (51 exons spanning over 148 Kb) and the stringency of gene-level curation of the TCGA bioinformatics pipeline, only 93 cases with complete LRRK2 sequence were available. A total of 28 LRRK2 somatic variants (synonymous, non-synonymous, and deep intronic) were identified, of which 18 were considered potentially pathogenic in 17 cases, including 11 missense, 3 nonsense, 3 frameshift, and 1 splice-site variants (Table 1). LRRK2 encodes a multi-domain protein with an enzymatic core comprised of a Ras of complex (ROC) GTPase domain in tandem with a C-terminal of Roc (COR) domain and a kinase domain, that localizes to the cytoplasm and mitochondrial membrane. A large fraction of the alterations were stop-gain, inactivating mutations (41% of cases). Interestingly, missense variants commonly targeted the ROC, COR, and kinase domains (Table 1). A single case was characterized by the PD-associated LRRK2 p.G2385R mutation. Cases with wild-type/polymorphic variant LRRK2 sequences and cases with variants with insufficient evidence for pathogenicity are listed in Tables 2 and 3.

TABLE 3

Cases with LRRK2 DNA sequence information without pathogenic mutation

| Case Number | Harrod. |
|---|---|
| 18 | TCGA-3C-AAAU |
| 19 | TCGA-A1-A0SF |
| 20 | TCGA-A1-A0SO |
| 21 | TCGA-A2-A04P |
| 22 | TCGA-A2-A0TO |
| 23 | TCGA-A2-A0YM |
| 24 | TCGA-A2-A3XV |
| 25 | TCGA-A7-A4SC |
| 26 | TCGA-A7-A4SD |
| 27 | TCGA-A7-A6VW |
| 28 | TCGA-A8-A06R |
| 29 | TCGA-A8-A075 |
| 30 | TCGA-A8-A08F |
| 31 | TCGA-A8-A09G |
| 32 | TCGA-A8-A09Z |
| 33 | TCGA-A8-A0A7 |
| 34 | TCGA-AC-A62X |
| 35 | TCGA-AC-A7VB |
| 36 | TCGA-AN-A0AJ |
| 37 | TCGA-AN-A0AL |
| 38 | TCGA-AN-A0FL |
| 39 | TCGA-AO-A0J3 |
| 40 | TCGA-AR-A0TP |
| 41 | TCGA-AR-A0TS |
| 42 | TCGA-AR-A0TU |
| 43 | TCGA-AR-A0TX |
| 44 | TCGA-AR-A1AH |
| 45 | TCGA-AR-A1AR |
| 46 | TCGA-AR-A1AV |
| 47 | TCGA-AR-A24H |
| 48 | TCGA-AR-A24M |
| 49 | TCGA-AR-A256 |
| 50 | TCGA-B6-A0RI |
| 51 | TCGA-BH-A0AV |
| 52 | TCGA-BH-A0C1 |
| 53 | TCGA-BH-A0DD |
| 54 | TCGA-BH-A0DG |
| 55 | TCGA-BH-A0DX |
| 56 | TCGA-BH-A0E0 |
| 57 | TCGA-BH-A0H9 |
| 58 | TCGA-BH-A0HF |
| 59 | TCGA-BH-A0WA |
| 60 | TCGA-BH-A18Q |
| 61 | TCGA-BH-A18U |

TABLE 3-continued

Cases with LRRK2 DNA sequence information without pathogenic mutation

| Case Number | Harrod. |
|---|---|
| 62 | TCGA-BH-A18V |
| 63 | TCGA-BH-A1EO |
| 64 | TCGA-BH-A1FN |
| 65 | TCGA-C8-A12K |
| 66 | TCGA-C8-A12M |
| 67 | TCGA-C8-A12Q |
| 68 | TCGA-C8-A1HG |
| 69 | TCGA-C8-A1HN |
| 70 | TCGA-C8-A27B |
| 71 | TCGA-D8-A147 |
| 72 | TCGA-D8-A1JL |
| 73 | TCGA-D8-A1JM |
| 74 | TCGA-D8-A1XL |
| 75 | TCGA-D8-A1XQ |
| 76 | TCGA-D8-A27F |
| 77 | TCGA-E2-A14R |
| 78 | TCGA-E2-A15M |
| 79 | TCGA-E2-A1IO |
| 80 | TCGA-E2-A1L8 |
| 81 | TCGA-E2-A1LL |
| 82 | TCGA-E9-A22E |
| 83 | TCGA-E9-A5U0 |
| 84 | TCGA-EW-A1J5 |
| 85 | TCGA-EW-AIOY |
| 86 | TCGA-EW-A1P4 |
| 87 | TCGA-EW-A1PB |
| 88 | TCGA-GI-A2C8 |
| 89 | TCGA-HN-A2NL |
| 90 | TCGA-OL-A5D7 |
| 91 | TCGA-OL-A5RW |
| 92 | TCGA-PL-A8LV |
| 93 | TCGA-S3-AA10 |

All patients with tumors harboring LRRK2 mutations were female, had a median age at diagnosis of 61 (range, 41-90) years, and the majority presented with stage II or III disease (82%); these characteristics were similar to the study cohort (Table 4).

TABLE 4

Demographic characteristics of the TCGA-BRCA cohort, stratified by LRRK2 sequence status.

| Variable | TCGA-BRCA (N = 1,098) | LRR1C2 Not Mutated (N = 76) | LRRK2 Mutated (N = 1.7) | P-Value |
|---|---|---|---|---|
| Age [Median (range)] | 59 (27-90) | 59 (31-84) | 61 (41-90) | P = 0 056 |
| Sex | | | | |
| Female | 1.085 (99) | 74 (97) | 17 (100) | P = 0 499 |
| Male | 12 (1) | 2 (3) | 0 (0) | |
| Menopausal Status | | | | |
| Pre- | 299 (21) | 20 (31) | 1 (6) | P = 0.086 |
| Peri- | 39 (4) | 1 (2) | 1 (6) | |
| Post- | 705 (64) | 43 (67) | 14 (88) | |
| Race/Ethnicity | | | | |
| White | 757 (69) | 46 (69) | 13 (77) | P = 0.611 |
| Black or AA | 183 (17) | 15 (22) | 2 (12) | |
| Asian | 61 (6) | 6 (9) | 2 (12) | |
| Hispanic | 39 (4) | 3 (5) | 0 (0) | P = 0.357 |
| AJCC Stage* | | | | |
| | 183 (17) | 5 (7) | 3 (18) | P = 0.330 |
| II | 621 (57) | 53 (72) | 10 (59) | |
| III | 249 (23) | 16 (22) | 4 (23) | |
| IV | 20 (2) | 0 (0) | 0 (0) | |

TABLE 4-continued

Demographic characteristics of the TCGA-BRCA cohort, stratified by LRRK2 sequence status.

| Variable | TCGA-BRCA (N = 1,098) | LRR1C2 Not Mutated (N = 76) | LRRK2 Mutated (N = 1.7) | P-Value |
|---|---|---|---|---|
| Predictive Biomarkers | | | | |
| ER( + ), PR ( + ), HER2 (−) | 482 (44) | 21 (33) | 5 (36) | P = 0.714 |
| ER( + ), PR (−), HER2 (−) | 91 (8) | 7 (11) | 2 (14) | |
| ER(−), PR (−), HER2 ( + ) | 39 (4) | 4 (6) | 0 (0) | |

TABLE 4-continued

Demographic characteristics of the TCGA-BRCA cohort, stratified by LRRK2 sequence status.

| Variable | TCGA-BRCA (N = 1,098) | LRR1C2 Not Mutated (N = 76) | LRRK2 Mutated (N = 1.7) | P-Value |
|---|---|---|---|---|
| ER( + ), PR (−), HER2 ( + ) | 32 (3) | 3 (5) | 2 (14) | |
| ER( + ), PR ( + ), HER2 ( + ) | 111 (10) | 6 (9) | 1 (7) | |
| ER(−), PR (−), HER2 (−) | 146 (13) | 23 (36) | 4 (29) | |

*As reported, including AJCC $3^{rd}$-$7^{th}$ editions.
[1]Values are reported as n (%).

TABLE 5

Clinicopathologic summary of breast cancer patients harboring a LRRK2 mutation.

| Case | Age | Histology | Grade | Laterality | Quadrant | pT | pN | pM | Stage[a] |
|---|---|---|---|---|---|---|---|---|---|
| 1 | 52 | Ductal with apocrine features and zonal necrosis | 3 | Right | UIQ | T2 | N0 | M0 | IIA |
| 2 | 77 | Ductal with apocrine and micropapillary features and zonal necrosis | 3 | Left | UOQ | T2 | N0 | M0 | IIA |
| 3 | 90 | Ductal with apocrine features | 3 | Right | UIQ. LIQ | T2 | NX | M0 | IIA |
| 4 | 56 | Ductal with apocrine features | 3 | Left | NOS | T2 | N1 | M0 | IIB |
| 5 | 69 | Ductal with apocrine features | 3 | Right | LIQ | T2 | N0 | M0 | IIA |
| 6 | 74 | Ductal with clear cell features | 3 | Left | UIQ | T1 | N0 | M0 | LA |
| 7 | 81 | Ductal with apocrine features and zonal necrosis | 3 | Right | UOQ. LIQ | T2 | N3 | MX | IIIC |
| 8 | 53 | Pleomorphic lobular with apocrine features | 3 | Right | NOS | T2 | N1 | M0 | IIB |
| 9 | 55 | Ductal with prominent lymphocytic infiltrate and zonal necrosis | 3 | Left | LIQ | T2 | N1 | MX | IIB |
| 10 | 59 | Ductal with apocrine and cribriform features | 2 | Left | UOQ | T2 | N1 | M0 | IIIA |
| 11 | 141 | Ductal with prominent lymphocytic infiltrate and zonal necrosis | 3 | Left | UOQ | T1 | N0 | M0 | IA |
| 12 | 55 | Ductal with clear cell features and zonal necrosis | 3 | Left | UOQ | T2 | N0 | M0 | IIA |
| 13 | 82 | Ductal with apocrine features prominent lymphocytic infiltrate and zonal necrosis | 3 | Right | LIQ | T1 | N2 | M0 | IIA |
| 14 | 68 | Ductal, NOS | 3 | Right | NOS | T2 | N0 | M0 | IIA |
| 15 | 61 | Pleomorphic lobular with apocrine features | 2 | Left | UIQ | T4 | N0 | M0 | IIIB |
| 16 | 47 | Ductal with apocrine features | 3 | Right | UIQ | T1 | NX | M0 | IA |
| 17 | 80 | Pleomorphic lobular with apocrine features | | Right | NOS | T2 | N1 | MX | IIB |

Abbreviations: Not otherwise specified, NOS; upper outer quadrant, UOQ; upper inner quadrant, UIQ; lower outer quadrant, LOQ; lower inner quadrant, LIQ.
[a]Staging information per AJCC 8th edition.

In Table 5, 82% of the tumors in Table 5 were high-grade, Nottingham grade 3 and 18% tumor were ductal and pleomorphic lobular morphologies prevailed.

Interestingly, a granular eosinophilic cytoplasm, consistent with mitochondrial-rich apocrine-like features, was present in 71% of LRRK2-mutated cases (4 cases were triple-negative, and no case was positive for HER2 in the absence of ER expression (FIG. 1A, Table 2). Clinical predictive marker information was available for 15 patients with LRRK2 mutations. Most cases were estrogen receptor (ER)-positive disease (67%), including 3 cases that were additionally positive for human epidermal growth factor receptor 2 (HER2, Table 4). Androgen receptor expression information was not available.

To explore the genomic landscape of LRRK2-mutated tumors (i.e., tumor comprising one or more LRRK2 mutations), we assessed for single nucleotide variants and copy number changes in commonly altered genes in breast cancer. TP53 alterations, including stop-gain mutations and copy number losses, were the most common event (65%, Table 2).

Figure 3:
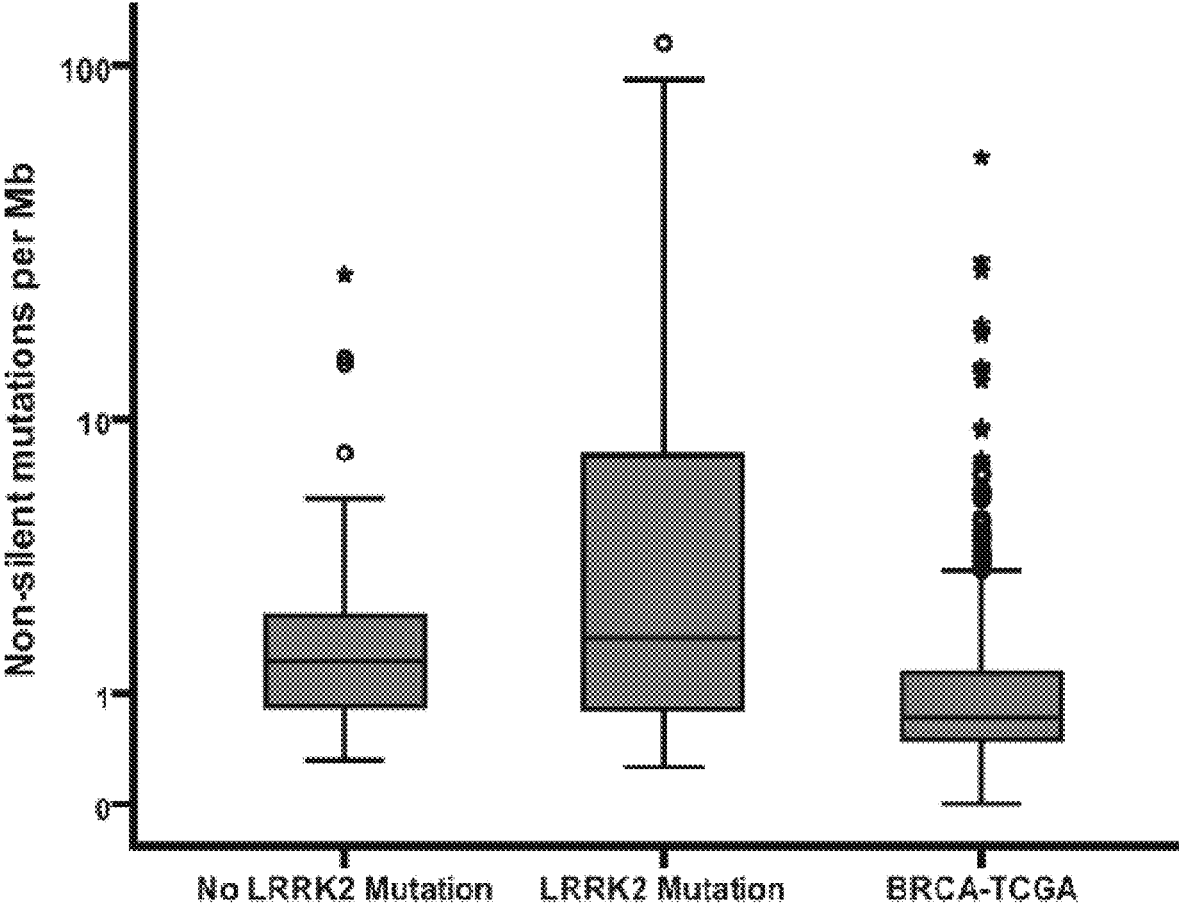
FIG. 3 is a graph showing tumor mutation burden in LRRK2-mutated carcinomas in accordance with one embodiment of the present disclosure. Box-plot of non-silent mutations per megabase of DNA in tumors with LRRK2 mutations (N=16) compared to cases with no LRRK2 mutations (N=69) and the remainder of the TCGA-BRCA cohort (N=903). The mean mutation burden among cases with a confirmed LRRK2 pathogenic mutation compared with those with LRRK2 sequence information but without a pathogenic mutation or the BRCA-TCGA cohort was 16.6 versus 2.2 non-silent mutations per Mb, respectively; Mann-Whitney P=0.377. Comparing the mean mutation burden among cases with a confirmed LRRK2 pathogenic mutation to the TCGA-BRCA cohort was 16.6 versus 1.3 non-silent mutations per Mb, respectively; Mann-Whiney P=0.002. Circles (°) represent outliers (1.5 times interquartile range) and stars (*) represent extreme outliers, as defined as 3 times the interquartile range.

Furthermore, LRRK2-mutated carcinomas displayed a high mutation burden compared to the remainder of the breast cancer cohort (mean 16.6 vs. 1.4 non-silent mutations per Mb, respectively; Mann-Whitney P=0.003, FIG. 1B). In fact, the two cases with the highest tumor mutation burdens in the TCGA-BRCA harbored LRRK2 mutations. LRRK2-mutated carcinomas showed similarly high mutation burdens when only cases with complete LRRK2 sequence were considered, despite the small sample size (FIG. 3).

Figure 4:
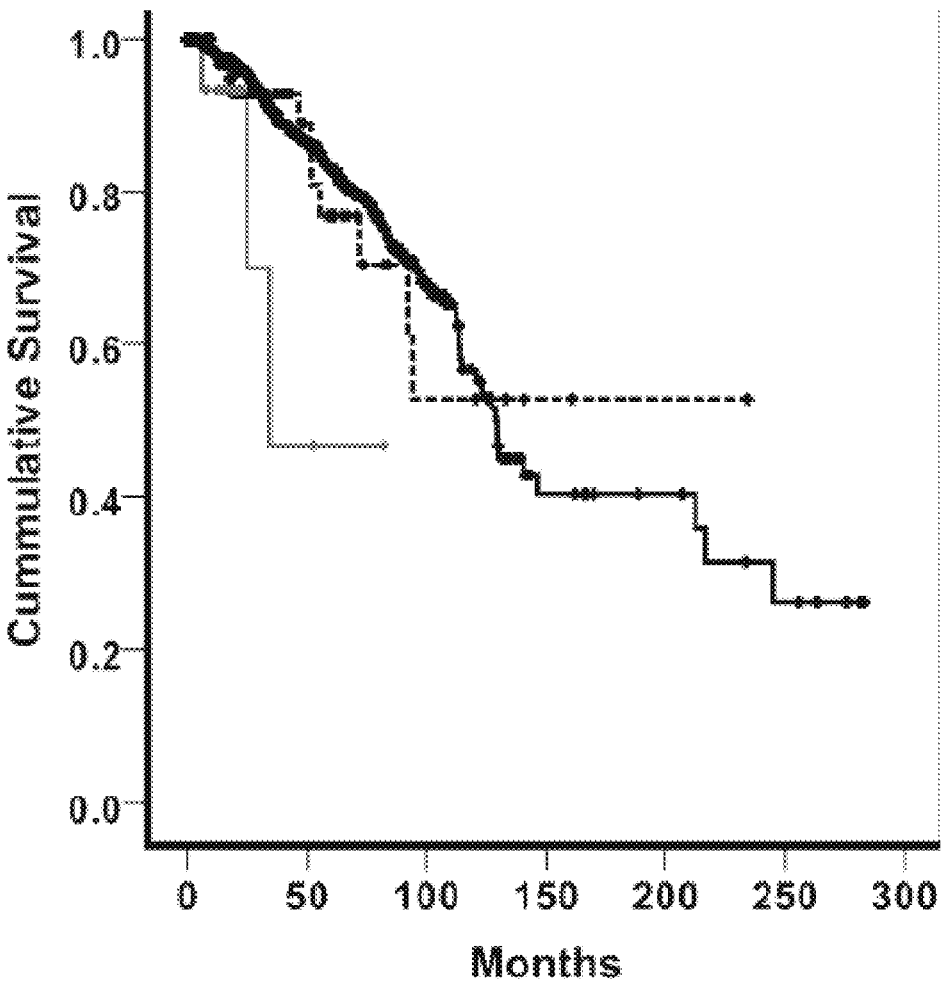
FIG. 4 is a graph showing Kaplan-Meier overall survival (OS) stratified by LRRK2 mutation status in accordance with one embodiment of the present disclosure. Patients with tumors harboring a LRRK2 mutation (grey line; N=17) display an OS inferior to patients relative to both those with LRRK2 sequence and no pathogenic mutation (dashed line; N=76) and those with indeterminate LRRK2 status (black line; N=1,003). The 3-year OS rates were 47%, 93% and 90%, respectively, with the overall Log-Rank P=0.082.

Consistent with a high-risk phenotype, subjects with LRRK2 mutations had a statistically significant inferior overall survival, including three-year survival rates of 31% and 84% among patients with a LRRK2 mutations and the remainder of the TGCA-BRCA, respectively, with a hazard ratio of 3.42 (95% CI=1.08-10.80, P=0.036, FIG. 1C). Similar overall survival trends were observed when LRRK2-sequenced cases alone were examined, albeit this study was under-powered (FIG. 4).

C. Discussion

We uncovered a previously unrecognized role of LRRK2 in breast cancer, whereby tumors harboring a somatic LRRK2 mutation may constitute a distinct clinicopathologic entity with increased tumor mutation burden and high-risk clinical behavior. Immune checkpoint inhibitors have emerged as effective oncologic therapy leveraging adaptive immune responses, and detecting error-prone DNA repair deficiencies predict responses to these drugs, presumably due to the production of mutation-associated neoantigens. As a corollary, tumor mutation burden has been used as a predictive biomarker in this therapeutic context, albeit with imperfect correlation with responses. Detailed biochemical studies will be necessary to dissect whether LRRK2 alterations are causative of increased mutation burdens or a sensitive marker of LRRK2-independent mutagenesis. Nonetheless, the high fraction of inactivating stop-gain mutations in LRRK2 would suggest a mechanistic relationship, not a bystander effect, and evidence exists supporting a DNA maintenance role for LRRK2. Assessing for LRRK2 integrity may thus identify a subset of genomically unstable breast tumors with vulnerability to immune checkpoint inhibition.

A recent study reported that PD patients with germline LRRK2 p.G2019S mutations were at an increased risk for leukemia and colon cancer, suggesting that the overall baseline cancer risk may be elevated among LRRK2 mutation carriers. Of note, a PD-associated variant, p.G2385R, was somatically detected in one breast cancer case, although the functional impact of this particular variant is still poorly understood. It will be informative to investigate whether LRRK2 mutations occur in other primary sites, supporting a broader tumor suppressor function for LRRK2 and future mechanistic studies may examine a direct role in cancer pathogenesis.

Several PD associated genes, including LRRK2, have been implicated in cell cycle control and tied to DNA integrity, which are classic tumor suppressor functions frequently targeted for inactivation in cancer. The somatic LRRK2 variants identified here were predicted to be loss-of-function, including a high proportion of stop-gain mutations, albeit biochemical functional characterizations are still necessary to substantiate the pathogenic nature of these variants. Yet, biochemical studies examining the common PD-linked p.G2019S mutation have described a gain-of-function, and clinical trial for PD using LRRK2 kinase inhibitors and antisense oligonucleotides are currently underway (clinicaltrials.gov). In light of our results, it may be prudent to assess the impact of LRRK2 dysregulation on carcinogenesis as a side effect of LRRK2-directed PD therapy.

One of the limitations of our study is that of the 1098 breast cancer cases in the TCGA, only a fraction had available LRRK2 sequence information, limiting the statistical power of our results. To address this, somatic LRRK2 pathogenic variants were identified in the cBio Cancer Genomics Portal in primary and metastatic breast cancer (Table 6), showing some overlap with the TCGA-BRCA, including another missense variant targeting leucine 425 and nonsense mutation p.S858*.

TABLE 6

| cBioPortal LRRK2 mutations, predicted protein change, variant type and domain affected. | | | | | | | |
|---|---|---|---|---|---|---|---|
| Sample ID | Study | Cancer Type | Coding | Protein | Variant Type | Domain | CNV |
| MO_1411 | Metastatic Solid Cancers | ILC | c.1274T > A | p.L425H | Missense | Armadillo | NA |
| PD4120a | Breast Invasive Carcinoma | IMC | c.2573C > G | p.S858* | Nonsense | Inter-domain | NA |
| MO_1384 | Metastatic Solid Cancers | IDC | c.2726dup | p.Asn909Lysfs*4 | Frameshift | Inter-domain | NA |
| MO_1190 | Metastatic Solid Cancers | ILC | c.4696G > A | p.E1566K | Missense | COR | NA |
| SA089 | Breast Invasive Carcinoma | IMC | c.6042G > C | p.K2014N | Missense | Kinase | NA |
| MBC_126 | Metastatic Breast Cancer | IMC | c.6119C > T | p.A2040V | Missense | Kinase | NA |

TABLE 6-continued cBioPortal LRRK2 mutations, predicted protein change, variant type and domain affected.

| Sample ID | Study | Cancer Type | Coding | Protein | Variant Type | Domain | CNV |
|---|---|---|---|---|---|---|---|
| SM-AZ5KE | The Metastatic Breast Cancer Project | IDC | c.6203C > A | p.T2068K | Missense | Kinase | NA |
| MBC_88 | Metastatic Breast Cancer | IMC | NA | NA | NA | NA | HD |
| MBC_96 | Metastatic Breast Cancer | IMC | NA | NA | NA | NA | HD |
| MBC_149 | Metastatic Breast Cancer | IMC | NA | NA | NA | INA | HD |
| MBC_166 | Metastatic Breast Cancer | IMC | NA | NA | NA | NA | HD |
| SM-AZ5JR | The Metastatic Breast Cancer Project | IDC | NA | NA | NA | NA | HD |
| SM-AZ5L1 | The Metastatic Breast Cancer Project | IMC | NA | NA | NA | NA | HD |
| SM-CGMAA | The Metastatic Breast Cancer Project | IDC | NA | NA | NA | NA | HD |
| SM-DL3UR. | The Metastatic Breast Cancer Project | IDC | NA | NA | NA | NA | HD |
| SM-CGLNA | The Metastatic Breast Cancer Project | IDC | NA | NA | NA | NA | HD |
| SM-DL3OH | The Metastatic Breast Cancer Project | DC | NA | NA | NA | NA | HD |
| SM-GQCIP | The Metastatic Breast Cancer Project | IMC | NA | NA | NA | NA | HD |

Abbreviations: Invasive ductal carcinoma, IDC; invasive lobular carcinoma, ILC; invasive mammary carcinoma not otherwise specified, IMC; Not applicable; NA; copy number variant, CNV; HD, homozygous deletion.
*denotes stop codon.

The fact that stop-gain mutations and homozygous deletions are reported in this external dataset additionally support our view that LRRK2 inactivation is a breast cancer-associated phenomenon (Table 6). Furthermore, as a retrospective study, we were limited by the paucity of clinical information available for the evaluation of therapeutic outcomes. Notwithstanding these limitations, the relative frequency of LRRK2 mutations detected is strong evidence for its biomedical and oncologic relevance. Based on our collective findings, the inclusion of LRRK2 in commercial somatic sequencing panels may be warranted.

In conclusion, somatic LRRK2 mutations are associated with breast cancer, and these findings shed light onto the mechanistic underpinnings of LRRK2-related neurodegeneration versus neoplastic disease. The identification of LRRK2 mutations in breast cancer may provide an opportunity for risk stratification and new treatment paradigms.

TABLE 7

Clinical Features of LRRK2 breast cancers

| Case | ID | Age | Histology | Grade | Laterality | Quadrant | pT | pN | pM | Stage |
|---|---|---|---|---|---|---|---|---|---|---|
| 1 | TCGA-E9-A243 | 52 | Ductal with apocrine features and zonal necrosis | 3 | Right | UIQ | T2 | N0 | M0 | IIA |
| 2 | TCGA-AN-A0AK | 77 | Ductal with apocrine and micropapillary features and zonal necrosis | 3 | Left | UOQ | T2 | N0 | M0 | IIA |
| 3 | TCGA-AC-A23H | 90 | Ductal with apocrine features | 3 | Right | UIQ, LIQ | T2 | NX | M0 | IIA |
| 4 | TCGA-C8-A132 | 56 | Ductal with apocrine features | 3 | Left | NOS | T2 | N1 | M0 | IIB |
| 5 | TCGA-AN-A046 | 69 | Ductal with apocrine features | 3 | Right | LIQ | T2 | NO | M0 | IIA |
| 6 | TCGA-D8-A1JP | 74 | Ductal with clear cell features | 3 | Left | UIQ | T1 | NO | M0 | IA |
| 7 | TCGA-D8-A1X5 | 81 | Ductal with apocrine features and zonal necrosis | 3 | Right | UOQ, LIQ | T2 | N3 | MX | IIIC |
| 8 | TCGA-BH-A0E9 | 53 | Pleomorphic lobular with apocrine features | 3 | Right | NOS | T2 | N1 | M0 | IIB |

TABLE 7-continued

| | | | Clinical Features of LRRK2 breast cancers | | | | | | | |
|---|---|---|---|---|---|---|---|---|---|---|
| Case | ID | Age | Histology | Grade | Laterality | Quadrant | pT | pN | pM | Stage |
| 9 | TCGA-D8-A1XK | 55 | Ductal with prominent lymphocytic infiltrate and zonal necrosis | 3 | Left | LIQ | T2 | N1 | MX | IIB |
| 10 | TCGA-AN-A0XO | 59 | Ductal with apocrine and focal cribriform features | 2 | Left | UOQ | T2 | N1 | M0 | IIIA |
| 11 | TCGA-AO-A0J4 | 41 | Ductal with prominent lymphocytic infiltrate and zonal necrosis | 3 | Left | UOQ | T1 | N0 | M0 | IA |
| 12 | TCGA-AN-A0XU | 55 | Ductal with clear cell features and zonal necrosis | 3 | Left | UOQ | T2 | N0 | M0 | IIA |
| 13 | TCGA-D8-A1XZ | 82 | Ductal with apocrine and cribriform features and zonal necrosis | 3 | Right | LIQ | T1 | N2 | M0 | IIIA |
| 14 | TCGA-S3-AA11 | 68 | Ductal, NOS | 3 | Right | NOS | T2 | N0 | M0 | IIA |
| 15 | TCGA-C8-A3M7 | 61 | Pleomorphic lobular with apocrine features | 2 | Left | UIQ | T4 | N0 | M0 | IIIB |
| 16 | TCGA-B6-A018 | 47 | Ductal with apocrine features | 3 | Right | UIQ | T1 | NX | M0 | IA |
| 17 | TCGA-AC-A3QP | 80 | Pleomorphic lobular with apocrine features | 2 | Right | NOS | T2 | N1 | MX | IIB |

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims. No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

Illustrative sequences:

| SEQ ID | Description | Sequences |
|---|---|---|
| SEQ ID NO: 1 | LRRK2 amino acid sequence | MASGSCQGCEEDEETLKKLIVRLNNVQEGKQIETLVQILEDLLVFTYSERASKLFQGKNI HVPLLIVLDSYMRVASVQQVGWSLLCKLIEVCPGTMQSLMGPQDVGNDWEVLGVHQLILK MLTVHNASVNLSVIGLKTLDLLLTSGKITLLILDEESDIFMLIFDAMHSFPANDEVQKLG CKALHVLFERVSEEQLTEFVENKDYMILLSALTNFKDEEEIVLHVLHCLHSLAIPCNNVE VLMSGNVRCYNIVVEAMKAFPMSERIQEVSCCLLHRLTLGNFFNILVLNEVHEFVVKAVQ QYPENAALQISALSCLALLTETIFLNQDLEEKNENQENDDEGEEDKLFWLEACYKALTWH RKNKHVQEAACWALNNLLMYQNSLHEKIGDEDGHFPAHREVMLSMLMHSSSKEVFQASAN ALSTLLEQNVNFRKILLSKGIHLNVLELMQKHIHSPEVAESGCKMLNHLFEGSNTSLDIM AAVVPKILTVMKRHETSLPVQLEALRAILHFIVPGMPEESREDTEFHHKLNMVKKQCFKN DIHKLVLAALNRFIGNPGIQKCGLKVISSIVHFPDALEMLSLEGAMDSVLHTLQMYPDDQ EIQCLGLSLIGYLITKKNVFIGTGHLLAKILVSSLYRFKDVAEIQTKGFQTILAILKLSA SFSKLLVHHSFDLVIFHQMSSNIMEQKDQQFLNLCCKCFAKVAMDDYLKNVMLERACDQN NSIMVECLLLLGADANQAKEGSSLICQVCEKESSPKLVELLLNSGSREQDVRKALTISIG KGDSQIISLLLRRLALDVANNSICLGGFCIGKVEPSWLGPLFPDKTSNLRKQTNIASTLA RMVIRYQMKSAVEEGTASGSDGNFSEDVLSKFDEWTFIPDSSMDSVFAQSDDLDSEGSEG SFLVKKKSNSISVGEFYRDAVLQRCSPNLQRHSNSLGPIFDHEDLLKRKRKILSSDDSLR SSKLQSHMRHSDSISSLASEREYITSLDLSANELRDIDALSQKCCISVHLEHLEKLELHQ NALTSFPQQLCETLKSLTHLDLHSNKFTSFPSYLLKMSCIANLDVSRNDIGPSVVLDPTV KCPTLKQFNLSYNQLSFVPENLTDVVEKLEQLILEGNKISGICSPLRLKELKILNLSKNH ISSLSENFLEACPKVESFSARMNFLAAMPFLPPSMTILKLSQNKFSCIPEAILNLPHLRS LDMSSNDIQYLPGPAHWKSLNLRELLFSHNQISILDLSEKAYLWSRVEKLHLSHNKLKEI PPEIGCLENLTSLDVSYNLELRSFPNEMGKLSKIWDLPLDELHLNFDFKHIGCKAKDIIR FLQQRLKKAVPYNRMKLMIVGNTGSGKTTLLQQLMKTKKSDLGMQSATVGIDVKDWPIQI RDKRKRDLVLNVWDFAGREEFYSTHPHFMTQRALYLAVYDLSKGQAEVDAMKPWLFNIKA RASSSPVILVGTHLDVSDEKQRKACMSKITKELLNKRGFPAIRDYHFVNATEESDALAKL RKTIINESLNFKIRDQLVVGQLIPDCYVELEKIILSERKNVPIEFPVIDRKRLLQLVREN QLQLDENELPHAVHFLNESGVLLHFQDPALQLSDLYFVEPKWLCKIMAQILTVKVEGCPK HPKGIISRRDVEKFLSKKRKFPKNYMSQYFKLLEKFQIALPIGEEYLLVPSSLSDHRPVI ELPHCENSEIIIRLYEMPYFPMGFWSRLINRLLEISPYMLSGRERALRPNRMYWRQGIYL NWSPEAYCLVGSEVLDNHPESFLKITVPSCRKGCILLGQVVDHIDSLMEEWFPGLLEIDI |

-continued

Illustrative sequences:

| SEQ ID | Description | Sequences |
|--------|-------------|-----------|
| | | CGEGETLLKKWALYSFNDGEEHQKILLDDLMKKAEEGDLLVNPDQPRLTIPISQIAPDLI |
| | | LADLPRNIMLNNDELEFEQAPEFLLGDGSFGSVYRAAYEGEEVAVKIFNKHTSLRLLRQE |
| | | LVVLCHLHHPSLISLLAAGIRPRMLVMELASKGSLDRLLQQDKASLTRTLQHRIALHVAD |
| | | GLRYLHSAMIIYRDLKPHNVLLFTLYPNAAIIAKIADYGIAQYCCRMGIKTSEGTPGFRA |
| | | PEVARGNVIYNQQADVYSFGLLLYDILTTGGRIVEGLKFPNEFDELEIQGKLPDPVKEYG |
| | | CAPWPMVEKLIKQCLKENPQERPTSAQVFDILNSAELVCLTRRILLPKNVIVECMVATHH |
| | | NSRNASIWLGCGHTDRGQLSFLDLNTEGYTSEEVADSRILCLALVHLPVEKESWIVSGTQ |
| | | SGTLLVINTEDGKKRHTLEKMTDSVTCLYCNSFSKQSKQKNFLLVGTADGKLAIFEDKTV |
| | | KLKGAAPLKILNIGNVSTPLMCLSESTNSTERNVMWGGCGTKIFSFSNDFTIQKLIETRT |
| | | SQLFSYAAFSDSNIITVVVDTALYIAKQNSPVVEVWDKKTEKLCGLIDCVHFLREVMVKE |
| | | NKESKHKMSYSGRVKTLCLQKNTALWIGTGGGHILLLDLSTRRLIRVIYNFCNSVRVMMT |
| | | AQLGSLKNVMLVLGYNRKNTEGTQKQKEIQSCLTVWDINLPHEVQNLEKHIEVRKELAEK |
| | | MRRTSVE |
| SEQ ID NO: 2 | LRRK2 nucleic acid sequence | ATGGCTAGTGGCAGCTGTCAGGGGTGCGAAGAGGACGAGGAAACTCTGAA |
| | | GAAGTTGATAGTCAGGCTGAACAATGTCCAGGAAGGAAAACAGATAGAAA |
| | | CGCTGGTCCAAATCCTGGAGGATCTGCTGGTGTTCACGTACTCCGAGCGC |
| | | GCCTCCAAGTTATTTCAAGGCAAAAATATCCATGTGCCTCTGTTGATCGT |
| | | CTTGGACTCCTATATGAGAGTCGCGAGTGTGCAGCAGGTGGGTTGGTCAC |
| | | TTCTGTGCAAATTAATAGAAGTCTGTCCAGGTACAATGCAAAGCTTAATG |
| | | GGACCCCAGGATGTTGGAAATGATTGGGAAGTCCTTGGTGTTCACCAATT |
| | | GATTCTTAAAATGCTAACAGTTCATAATGCCAGTGTAAACTTGTCAGTGA |
| | | TTGGACTGAAGACCTTAGATCTCCTCCTAACTTCAGGTAAAATCACCTTG |
| | | CTGATATTGGATGAAGAAAGTGATATTTTCATGTTAATTTTTGATGCCAT |
| | | GCACTCATTTCCAGCCAATGATGAAGTCCAGAAACTTGGATGCAAAGCTT |
| | | TACATGTGCTGTTTGAGAGAGTCTCAGAGGAGCAACTGACTGAATTTGTT |
| | | GAGAACAAAGATTATATGATATTGTTAAGTGCGTTAACAAATTTTAAAGA |
| | | TGAAGAGGAAATTGTGCTTCATGTGCTGCATTGTTTACATTCCCTAGCGA |
| | | TTCCTTGCAATAATGTGGAAGTCCTCATGAGTGGCAATGTCAGGTGTTAT |
| | | AATATTGTGGTGGAAGCTATGAAAGCATTCCCTATGAGTGAAAGAATTCA |
| | | AGAAGTGAGTTGCTGTTTGCTCCATAGGCTTACATTAGGTAATTTTTTCA |
| | | ATATCCTGGTATTAAACGAAGTCCATGAGTTTGTGGTGAAAGCTGTGCAG |
| | | CAGTACCCAGAGAATGCAGCATTGCAGATCTCAGCGCTCAGCTGTTTGGC |
| | | CCTCCTCACTGAGACTATTTTCTTAAATCAAGATTTAGAGGAAAAGAATG |
| | | AGAATCAAGAGAATGATGATGAGGGGGAAGAAGATAAATTGTTTTGGCTG |
| | | GAAGCCTGTTACAAAGCATTAACGTGGCATAGAAAGAACAAGCACGTGCA |
| | | GGAGGCCGCATGCTGGGCACTAAATAATCTCCTTATGTACCAAAACAGTT |
| | | TACATGAGAAGATTGGAGATGAAGATGGCCATTTCCCAGCTCATAGGGAA |
| | | GTGATGCTCTCCATGCTGATGCATTCTTCATCAAAGGAAGTTTTTCCAGGC |
| | | ATCTGCGAATGCATTGTCAACTCTCTTAGAACAAAATGTTAATTTCAGAA |
| | | AAATACTGTTATCAAAAGGAATACACCTGAATGTTTTGGAGTTAATGCAG |
| | | AAGCATATACATTCTCCTGAAGTGGCTGAAAGTGGCTGTAAAATGCTAAA |
| | | TCATCTTTTTGAAGGAAGCAACACTTCCCTGGATATAATGGCAGCAGTGG |
| | | TCCCCAAAATACTAACAGTTATGAAACGTCATGAGACATCATTACCAGTG |
| | | CAGCTGGAGGCGCTTCGAGCTATTTTACATTTTATAGTGCCTGGCATGCC |
| | | AGAAGAATCCAGGGAGGATACAGAATTTCATCATAAGCTAAATATGGTTA |
| | | AAAAACAGTGTTTCAAGAATGATATTCACAAACTGGTCCTAGCAGCTTTG |
| | | AACAGGTTCATTGGAAATCCTGGGATTCAGAAATGTGGATTAAAAGTAAT |
| | | TTCTTCTATTGTACATTTTCCTGATGCATTAGAGATGTTATCCCTGGAAG |
| | | GTGCTATGGATTCAGTGCTTCACACACTGCAGATGTATCCAGATGACCAA |
| | | GAAATTCAGTGTCTGGGTTTAAGTCTTATAGGATACTTGATTACAAAGAA |
| | | GAATGTGTTCATAGGAACTGGACATCTGCTGGCAAAAATTCTGGTTTCCA |
| | | GCTTATACCGATTTAAGGATGTTGCTGAAATACAGACTAAAGGATTTCAG |
| | | ACAATCTTAGCAATCCTCAAATTGTCAGCATCTTTTTCTAAGCTGCTGGT |
| | | GCATCATTCATTTGACTTAGTAATATTCCATCAAATGTCTTCCAATATCA |
| | | TGGAACAAAAGGATCAACAGTTTCTAAACCTCTGTTGCAAGTGTTTTGCA |
| | | AAAGTAGCTATGGATGATTACTTAAAAAATGTGATGCTAGAGAGAGCGTG |
| | | TGATCAGAATAACAGCATCATGGTTGAATGCTTGCTTCTATTGGGAGCAG |
| | | ATGCCAATCAAGCAAAGGAGGGATCTTCTTTAATTTGTCAGGTATGTGAG |
| | | AAAGAGAGCAGTCCCAAATTGGTGGAACTCTTACTGAATAGTGGATCTCG |
| | | TGAACAAGATGTACGAAAAGCGTTGACGATAAGCATTGGGAAAGGTGACA |
| | | GCCAGATCATCAGCTTGCTCTTAAGGAGGCTGGCCCTGGATGTGGCCAAC |
| | | AATAGCATTTGCCTTGGAGGATTTTGTATAGGAAAAGTTGAACCTTCTTG |
| | | GCTTGGTCCTTTATTTCCAGATAAGACTTCTAATTTAAGGAAACAAACAA |
| | | ATATAGCATCTACACTAGCAAGAATGGTGATCAGATATCAGATGAAAAGT |
| | | GCTGTGGAAGAAGGAACAGCCTCAGGCAGCGATGGAAATTTTTCTGAAGA |
| | | TGTGCTGTCTAAATTTGATGAATGGACCTTTATTCCTGACTCTTCTATGG |
| | | ACAGTGTGTTTGCTCAAAGTGATGACCTGGATAGTGAAGGAAGTGAAGGC |
| | | TCATTTCTTGTGAAAAAGAAATCTAATTCAATTAGTGTAGGAGAATTTTA |
| | | CCGAGATGCCGTATTACAGCGTTGCTCACCAAATTTGCAAAGACATTCCA |
| | | ATTCCTTGGGGCCCATTTTTGATCATGAAGATTTACTGAAGCGAAAAAGA |
| | | AAAATATTATCTTCAGATGATTCACTCAGGTCATCAAAAACTTCAATCCCA |
| | | TATGAGGCATTCAGACAGCATTTCTTCTCTGGCTTCTGAGAGAGAATATA |
| | | TTACATCACTAGACCTTTCAGCAAATGAACTAAGAGATATTGATGCCCTA |

-continued

Illustrative sequences:

SEQ
ID    Description          Sequences

AGCCAGAAATGCTGTATAAGTGTTCATTTGGAGCATCTTGAAAAGCTGGA
GCTTCACCAGAATGCACTCACGAGCTTTCCACAACAGCTATGTGAAACTC
TGAAGAGTTTGACACATTTGGACTTGCACAGTAATAAATTTACATCATTT
CCTTCTTATTTGTTGAAAATGAGTTGTATTGCTAATCTTGATGTCTCTCG
AAATGACATTGGACCCTCAGTGGTTTTAGATCCTACAGTGAAATGTCCAA
CTCTGAAACAGTTTAACCTGTCATATAACCAGCTGTCTTTTGTACCTGAG
AACCTCACTGATGTGGTAGAGAAACTGGAGCAGCTCATTTTAGAAGGAAA
TAAAATATCAGGGATATGCTCCCCCTTGAGACTGAAGGAACTGAAGATTT
TAAACCTTAGTAAGAACCACATTTCATCCCTATCAGAGAACTTTCTTGAG
GCTTGTCCTAAAGTGGAGAGTTTCAGTGCCAGAATGAATTTTCTTGCTGC
TATGCCTTTCTTGCCTCCTTCTATGACAATCCTAAAATTATCTCAGAACA
AATTTTCCTGTATTCCAGAAGCAATTTTAAATCTTCCACACTTGCGGTCT
TTAGATATGAGCAGCAATGATATTCAGTACCTACCAGGTCCCGCACACTG
GAAATCTTTGAACTTAAGGGAACTCTTATTTAGCCATAATCAGATCAGCA
TCTTGGACTTGAGTGAAAAGCATATTTATGGTCTAGAGTAGAGAAACTG
CATCTTTCTCACAATAAACTGAAAGAGATTCCTCCTGAGATTGGCTGTCT
TGAAAATCTGACATCTCTGGATGTCAGTTACAACTTGGAACTAAGATCCT
TTCCCAATGAAATGGGGAAATTAAGCAAAATATGGGATCTTCCTTTGGAT
GAACTGCATCTTAACTTTGATTTTAAACATATAGGATGTAAAGCCAAAGA
CATCATAAGGTTTCTTCAACAGCGATTAAAAAAGGCTGTGCCTTATAACC
GAATGAAACTTATGATTGTGGGAAATACTGGGAGTGGTAAAACCACCTTA
TTGCAGCAATTAATGAAAACCAAGAAATCAGATCTTGGAATGCAAAGTGC
CACAGTTGGCATAGATGTGAAAGACTGGCCTATCCAAATAAGAGACAAAA
GAAAGAGAGATCTCGTCCTAAATGTGTGGGATTTTGCAGGTCGTGAGGAA
TTCTATAGTACTCATCCCCATTTTATGACGCAGCGAGCATTGTACCTTGC
TGTCTATGACCTCAGCAAGGGACAGGCTGAAGTTGATGCCATGAAGCCTT
GGCTCTTCAATATAAAGGCTCGCGCTTCTTCTTCCCCTGTGATTCTCGTT
GGCACACATTTGGATGTTTCTGATGAGAAGCAACGCAAAGCCTGCATGAG
TAAAATCACCAAGGAACTCCTGAATAAGCGAGGGTTCCCTGCCATACGAG
ATTACCACTTTGTGAATGCCACCGAGGAATCTGATGCTTTGGCAAAACTT
CGGAAAACCATCATAAACGAGAGCCTTAATTTCAAGATCCGAGATCAGCT
TGTTGTTGGACAGCTGATTCCAGACTGCTATGTAGAACTTGAAAAAAATCA
TTTTATCGGAGCGTAAAAATGTGCCAATTGAATTTCCCGTAATTGACCGG
AAACGATTATTACAACTAGTGAGAGAAAATCAGCTGCAGTTAGATGAAAA
TGAGCTTCCTCACGCAGTTCACTTTCTAAATGAATCAGGAGTCCTTCTTC
ATTTTCAAGACCCAGCACTGCAGTTAAGTGACTTGTACTTTGTGGAACCC
AAGTGGCTTTGTAAAATCATGGCACAGATTTTGACAGTGAAAGTGGAAGG
TTGTCCAAAACACCCTAAGGGCATTATTTCGCGTAGAGATGTGGAAAAAT
TTCTTTCAAAAAAAAGGAAATTTCCAAAGAACTACATGTCACAGTATTTT
AAGCTCCTAGAAAAATTCCAGATTGCTTTGCCAATAGGAGAAGAATATTT
GCTGGTTCCAAGCAGTTTGTCTGACCACAGGCCTGTGATAGAGCTTCCCC
ATTGTGAGAACTCTGAAATTATCATCCGACTATATGAAATGCCTTATTTT
CCAATGGGATTTTGGTCAAGATTAATCAATCGATTACTTGAGATTTCACC
TTACATGCTTTCAGGGAGAGAACGAGCACTTCGCCCAAACAGAATGTATT
GGCGACAAGGCATTTACTTAAATTGGTCTCCTGAAGCTTATTGTCTGGTA
GGATCTGAAGTCTTAGACAATCATCCAGAGAGTTTCTTAAAAATTACAGT
TCCTTCTTGTAGAAAAGGCTGTATTCTTTTGGGCCAAGTTGTGGACCACA
TTGATTCTCTCATGGAAGAATGGTTTCCTGGGTTGCTGGAGATTGATATT
TGTGGTGAAGGAGAAACTCTGTTGAAGAAATGGGCATTATATAGTTTTAA
TGATGGTGAAGAACATCAAAAAATCTTACTTGATGACTTGATGAAGAAAG
CAGAGGAAGGAGATCTCTTAGTAAATCCAGATCAACCAAGGCTCACCATT
CCAATATCTCAGATTGCCCCTGACTTGATTTTGGCTGACCTGCCTAGAAA
TATTATGTTGAATAATGATGAGTTGGAATTTGAACAAGCTCCAGAGTTTC
TCCTAGGTGATGGCAGTTTTGGATCAGTTTACCGAGCAGCCTATGAAGGA
GAAGAAGTGGCTGTGAAGATTTTTAATAAACATACATCACTCAGGCTGTT
AAGACAAGAGCTTGTGGTGCTTTGCCACCTCCACCACCCCAGTTTGATAT
CTTTGCTGGCAGCTGGGATTCGTCCCCGGATGTGGTGATGGAGTTAGCC
TCCAAGGGTTCCTTGGATCGCCTGCTTCAGCAGGACAAAGCCAGCCTCAC
TAGAACCCTACAGCACAGGATTGCACTCCACGTAGCTGATGGTTTGAGAT
ACCTCCACTCAGCCATGATTATATACCGAGACCTGAAACCCCACAATGTG
CTGCTTTTCACACTGTATCCCAATGCTGCCATCATTGCAAAGATTGCTGA
CTACGGCATTGCTCAGTACTGCTGTAGAATGGGGATAAAAACATCAGAGG
GCACACCAGGGTTTCGTGCACCTGAAGTTGCCAGAGGAAATGTCATTTAT
AACCAACAGGCTGATGTTTATTCATTTGGTTTACTACTCTATGACATTTT
GACAACTGGAGGTAGAATAGTAGAGGGTTTGAAGTTTCCAAATGAGTTTG
ATGAATTAGAAATACAAGGAAAATTACCTGATCCAGTTAAAGAATATGGT
TGTGCCCCATGGCCTATGGTTGAGAAATTAATTAAACAGTGTTTGAAAGA
AAATCCTCAAGAAAGGCCTACTTCTGCCCAGGTCTTTGACATTTTGAATT
CAGCTGAATTAGTCTGTCTGACGAGACGCATTTTATTACCTAAAAACGTA
ATTGTTGAATGCATGGTTGCTACACATCACAACAGCAGGAATGCAAGCAT
TTGGCTGGGCTGTGGGCACACCGACAGAGGACAGCTCTCATTTCTTGACT
TAAATACTGAAGGATACACTTCTGAGGAAGTTGCTGATAGTAGAATATTG
TGCTTAGCCTTGGTGCATCTTCCTGTTGAAAAGGAAAGCTGGATTGTGTC
TGGGACACAGTCTGGTACTCTCCTGGTCATCAATACCGAAGATGGGAAAA

-continued

---

Illustrative sequences:

---

| SEQ ID | Description | Sequences |
|---|---|---|
| | | AGAGACATACCCTAGAAAAGATGACTGATTCTGTCACTTGTTTGTATTGC AATTCCTTTTCCAAGCAAAGCAAACAAAAAAATTTTCTTTTGGTTGGAAC CGCTGATGGCAAGTTAGCAATTTTTGAAGATAAGACTGTTAAGCTTAAAG GAGCTGCTCCTTTGAAGATACTAAATATAGGAAATGTCAGTACTCCATTG ATGTGTTTGAGTGAATCCACAAATTCAACGGAAAGAAATGTAATGTGGGG AGGATGTGGCACAAAGATTTTCTCCTTTTCTAATGATTTCACCATTCAGA AACTCATTGAGACAAGAACAAGCCAACTGTTTTCTTATGCAGCTTTCAGT GATTCCAACATCATAACAGTGGTGGTAGACACTGCTCTCTATATTGCTAA GCAAAATAGCCCTGTTGTGGAAGTGTGGGATAAGAAAACTGAAAAACTCT GTGGACTAATAGACTGCGTGCACTTTTTAAGGGAGGTAATGGTAAAAGAA AACAAGGAATCAAAACACAAATGTCTTATTCTGGGAGAGTGAAAACCCT CTGCCTTCAGAAGAACACTGCTCTTTGGATAGGAACTGGAGGAGGCCATA TTTTACTCCTGGATCTTTCAACTCGTCGACTTATACGTGTAATTTACAAC TTTTGTAATTCGGTCAGAGTCATGATGACAGCACAGCTAGGAAGCCTTAA AAATGTCATGCTGGTATTGGGCTACAACCGGAAAAATACTGAAGGTACAC AAAAGCAGAAAGAGATACAATCTTGCTTGACCGTTTGGGACATCAATCTT CCACATGAAGTGCAAAATTTAGAAAAACACATTGAAGTGAGAAAAGAATT AGCTGAAAAAATGAGACGAACATCTGTTGAGTAA |
| | The Armadillo domain | Amino acid residues 12-705 of SEQ ID NO: 1 (NP_940980.4) |
| | The Inter-domain | Amino acid residues 706-799 of SEQ ID NO: 1 (NP_940980.4) |
| | Leucine-rich repeat domain | Amino acid residues 800-1334 of SEQ ID NO: 1 (NP_940980.4) |
| | The ROC domain | Amino acid residues 1335-1511 of SEQ ID NO: 1 (NP_940980.4) |
| | The COR domain | Amino acid residues 1512-1879 of SEQ ID NO: 1 (NP_940980.4) |

---

SEQUENCE LISTING

---

<160> NUMBER OF SEQ ID NOS: 2

<210> SEQ ID NO 1
<211> LENGTH: 2527
<212> TYPE: PRT
<213> ORGANISM: Homo sapiens

<400> SEQUENCE: 1

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu Arg Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140
```

-continued

```
Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
            165                 170                 175

Gln Lys Leu Gly Cys Lys Ala Leu His Val Leu Phe Glu Arg Val Ser
                180             185             190

Glu Glu Gln Leu Thr Glu Phe Val Glu Asn Lys Asp Tyr Met Ile Leu
            195             200             205

Leu Ser Ala Leu Thr Asn Phe Lys Asp Glu Glu Glu Ile Val Leu His
        210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260             265             270

Leu Leu His Arg Leu Thr Leu Gly Asn Phe Phe Asn Ile Leu Val Leu
            275             280             285

Asn Glu Val His Glu Phe Val Val Lys Ala Val Gln Gln Tyr Pro Glu
        290             295             300

Asn Ala Ala Leu Gln Ile Ser Ala Leu Ser Cys Leu Ala Leu Leu Thr
305             310             315             320

Glu Thr Ile Phe Leu Asn Gln Asp Leu Glu Glu Lys Asn Glu Asn Gln
                325             330             335

Glu Asn Asp Asp Glu Gly Glu Glu Asp Lys Leu Phe Trp Leu Glu Ala
            340             345             350

Cys Tyr Lys Ala Leu Thr Trp His Arg Lys Asn Lys His Val Gln Glu
            355             360             365

Ala Ala Cys Trp Ala Leu Asn Asn Leu Leu Met Tyr Gln Asn Ser Leu
        370             375             380

His Glu Lys Ile Gly Asp Glu Asp Gly His Phe Pro Ala His Arg Glu
385             390             395             400

Val Met Leu Ser Met Leu Met His Ser Ser Ser Lys Glu Val Phe Gln
                405             410             415

Ala Ser Ala Asn Ala Leu Ser Thr Leu Leu Glu Gln Asn Val Asn Phe
            420             425             430

Arg Lys Ile Leu Leu Ser Lys Gly Ile His Leu Asn Val Leu Glu Leu
            435             440             445

Met Gln Lys His Ile His Ser Pro Glu Val Ala Glu Ser Gly Cys Lys
        450             455             460

Met Leu Asn His Leu Phe Glu Gly Ser Asn Thr Ser Leu Asp Ile Met
465             470             475             480

Ala Ala Val Val Pro Lys Ile Leu Thr Val Met Lys Arg His Glu Thr
                485             490             495

Ser Leu Pro Val Gln Leu Glu Ala Leu Arg Ala Ile Leu His Phe Ile
            500             505             510

Val Pro Gly Met Pro Glu Glu Ser Arg Glu Asp Thr Glu Phe His His
            515             520             525

Lys Leu Asn Met Val Lys Lys Gln Cys Phe Lys Asn Asp Ile His Lys
        530             535             540

Leu Val Leu Ala Ala Leu Asn Arg Phe Ile Gly Asn Pro Gly Ile Gln
545             550             555             560
```

-continued

```
Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
                580                 585                 590

Leu Gln Met Tyr Pro Asp Asp Gln Glu Ile Gln Cys Leu Gly Leu Ser
                595                 600                 605

Leu Ile Gly Tyr Leu Ile Thr Lys Lys Asn Val Phe Ile Gly Thr Gly
            610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
                675                 680                 685

Gln Gln Phe Leu Asn Leu Cys Cys Lys Cys Phe Ala Lys Val Ala Met
            690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Leu Asn Ser Gly Ser Arg Glu
                755                 760                 765

Gln Asp Val Arg Lys Ala Leu Thr Ile Ser Ile Gly Lys Gly Asp Ser
            770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
                820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
        850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
        930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975
```

-continued

```
Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
    1175                1180                1185

Pro Glu  Ala Ile Leu Asn Leu  Pro His Leu Arg Ser  Leu Asp Met
    1190                1195                1200

Ser Ser  Asn Asp Ile Gln Tyr  Leu Pro Gly Pro Ala  His Trp Lys
    1205                1210                1215

Ser Leu  Asn Leu Arg Glu Leu  Leu Phe Ser His Asn  Gln Ile Ser
    1220                1225                1230

Ile Leu  Asp Leu Ser Glu Lys  Ala Tyr Leu Trp Ser  Arg Val Glu
    1235                1240                1245

Lys Leu  His Leu Ser His Asn  Lys Leu Lys Glu Ile  Pro Pro Glu
    1250                1255                1260

Ile Gly  Cys Leu Glu Asn Leu  Thr Ser Leu Asp Val  Ser Tyr Asn
    1265                1270                1275

Leu Glu  Leu Arg Ser Phe Pro  Asn Glu Met Gly Lys  Leu Ser Lys
    1280                1285                1290

Ile Trp  Asp Leu Pro Leu Asp  Glu Leu His Leu Asn  Phe Asp Phe
    1295                1300                1305

Lys His  Ile Gly Cys Lys Ala  Lys Asp Ile Ile Arg  Phe Leu Gln
    1310                1315                1320

Gln Arg  Leu Lys Lys Ala Val  Pro Tyr Asn Arg Met  Lys Leu Met
    1325                1330                1335

Ile Val  Gly Asn Thr Gly Ser  Gly Lys Thr Thr Leu  Leu Gln Gln
    1340                1345                1350

Leu Met  Lys Thr Lys Lys Ser  Asp Leu Gly Met Gln  Ser Ala Thr
    1355                1360                1365
```

-continued

```
Val Gly  Ile Asp Val Lys Asp  Trp Pro Ile Gln Ile  Arg Asp Lys
    1370         1375          1380

Arg Lys  Arg Asp Leu Val Leu  Asn Val Trp Asp Phe  Ala Gly Arg
    1385         1390          1395

Glu Glu  Phe Tyr Ser Thr His  Pro His Phe Met Thr  Gln Arg Ala
    1400         1405          1410

Leu Tyr  Leu Ala Val Tyr Asp  Leu Ser Lys Gly Gln  Ala Glu Val
    1415         1420          1425

Asp Ala  Met Lys Pro Trp Leu  Phe Asn Ile Lys Ala  Arg Ala Ser
    1430         1435          1440

Ser Ser  Pro Val Ile Leu Val  Gly Thr His Leu Asp  Val Ser Asp
    1445         1450          1455

Glu Lys  Gln Arg Lys Ala Cys  Met Ser Lys Ile Thr  Lys Glu Leu
    1460         1465          1470

Leu Asn  Lys Arg Gly Phe Pro  Ala Ile Arg Asp Tyr  His Phe Val
    1475         1480          1485

Asn Ala  Thr Glu Glu Ser Asp  Ala Leu Ala Lys Leu  Arg Lys Thr
    1490         1495          1500

Ile Ile  Asn Glu Ser Leu Asn  Phe Lys Ile Arg Asp  Gln Leu Val
    1505         1510          1515

Val Gly  Gln Leu Ile Pro Asp  Cys Tyr Val Glu Leu  Glu Lys Ile
    1520         1525          1530

Ile Leu  Ser Glu Arg Lys Asn  Val Pro Ile Glu Phe  Pro Val Ile
    1535         1540          1545

Asp Arg  Lys Arg Leu Leu Gln  Leu Val Arg Glu Asn  Gln Leu Gln
    1550         1555          1560

Leu Asp  Glu Asn Glu Leu Pro  His Ala Val His Phe  Leu Asn Glu
    1565         1570          1575

Ser Gly  Val Leu Leu His Phe  Gln Asp Pro Ala Leu  Gln Leu Ser
    1580         1585          1590

Asp Leu  Tyr Phe Val Glu Pro  Lys Trp Leu Cys Lys  Ile Met Ala
    1595         1600          1605

Gln Ile  Leu Thr Val Lys Val  Glu Gly Cys Pro Lys  His Pro Lys
    1610         1615          1620

Gly Ile  Ile Ser Arg Arg Asp  Val Glu Lys Phe Leu  Ser Lys Lys
    1625         1630          1635

Arg Lys  Phe Pro Lys Asn Tyr  Met Ser Gln Tyr Phe  Lys Leu Leu
    1640         1645          1650

Glu Lys  Phe Gln Ile Ala Leu  Pro Ile Gly Glu Glu  Tyr Leu Leu
    1655         1660          1665

Val Pro  Ser Ser Leu Ser Asp  His Arg Pro Val Ile  Glu Leu Pro
    1670         1675          1680

His Cys  Glu Asn Ser Glu Ile  Ile Ile Arg Leu Tyr  Glu Met Pro
    1685         1690          1695

Tyr Phe  Pro Met Gly Phe Trp  Ser Arg Leu Ile Asn  Arg Leu Leu
    1700         1705          1710

Glu Ile  Ser Pro Tyr Met Leu  Ser Gly Arg Glu Arg  Ala Leu Arg
    1715         1720          1725

Pro Asn  Arg Met Tyr Trp Arg  Gln Gly Ile Tyr Leu  Asn Trp Ser
    1730         1735          1740

Pro Glu  Ala Tyr Cys Leu Val  Gly Ser Glu Val Leu  Asp Asn His
    1745         1750          1755
```

-continued

```
Pro Glu Ser Phe Leu Lys Ile Thr Val Pro Ser Cys Arg Lys Gly
    1760            1765            1770

Cys Ile Leu Leu Gly Gln Val Val Asp His Ile Asp Ser Leu Met
    1775            1780            1785

Glu Glu Trp Phe Pro Gly Leu Leu Glu Ile Asp Ile Cys Gly Glu
    1790            1795            1800

Gly Glu Thr Leu Leu Lys Lys Trp Ala Leu Tyr Ser Phe Asn Asp
    1805            1810            1815

Gly Glu Glu His Gln Lys Ile Leu Leu Asp Asp Leu Met Lys Lys
    1820            1825            1830

Ala Glu Glu Gly Asp Leu Leu Val Asn Pro Asp Gln Pro Arg Leu
    1835            1840            1845

Thr Ile Pro Ile Ser Gln Ile Ala Pro Asp Leu Ile Leu Ala Asp
    1850            1855            1860

Leu Pro Arg Asn Ile Met Leu Asn Asn Asp Glu Leu Glu Phe Glu
    1865            1870            1875

Gln Ala Pro Glu Phe Leu Leu Gly Asp Gly Ser Phe Gly Ser Val
    1880            1885            1890

Tyr Arg Ala Ala Tyr Glu Gly Glu Glu Val Ala Val Lys Ile Phe
    1895            1900            1905

Asn Lys His Thr Ser Leu Arg Leu Leu Arg Gln Glu Leu Val Val
    1910            1915            1920

Leu Cys His Leu His His Pro Ser Leu Ile Ser Leu Leu Ala Ala
    1925            1930            1935

Gly Ile Arg Pro Arg Met Leu Val Met Glu Leu Ala Ser Lys Gly
    1940            1945            1950

Ser Leu Asp Arg Leu Leu Gln Gln Asp Lys Ala Ser Leu Thr Arg
    1955            1960            1965

Thr Leu Gln His Arg Ile Ala Leu His Val Ala Asp Gly Leu Arg
    1970            1975            1980

Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu Tyr Asp Ile Leu Thr Thr Gly Gly Arg Ile
    2060            2065            2070

Val Glu Gly Leu Lys Phe Pro Asn Glu Phe Asp Glu Leu Glu Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Lys Gln Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Val Cys Leu Thr Arg Arg Ile Leu Leu Pro Lys
    2135            2140            2145
```

-continued

```
Asn Val  Ile Val Glu Cys Met  Val Ala Thr His His  Asn Ser Arg
    2150             2155             2160

Asn Ala  Ser Ile Trp Leu Gly  Cys Gly His Thr Asp  Arg Gly Gln
    2165             2170             2175

Leu Ser  Phe Leu Asp Leu Asn  Thr Glu Gly Tyr Thr  Ser Glu Glu
    2180             2185             2190

Val Ala  Asp Ser Arg Ile Leu  Cys Leu Ala Leu Val  His Leu Pro
    2195             2200             2205

Val Glu  Lys Glu Ser Trp Ile  Val Ser Gly Thr Gln  Ser Gly Thr
    2210             2215             2220

Leu Leu  Val Ile Asn Thr Glu  Asp Gly Lys Lys Arg  His Thr Leu
    2225             2230             2235

Glu Lys  Met Thr Asp Ser Val  Thr Cys Leu Tyr Cys  Asn Ser Phe
    2240             2245             2250

Ser Lys  Gln Ser Lys Gln Lys  Asn Phe Leu Leu Val  Gly Thr Ala
    2255             2260             2265

Asp Gly  Lys Leu Ala Ile Phe  Glu Asp Lys Thr Val  Lys Leu Lys
    2270             2275             2280

Gly Ala  Ala Pro Leu Lys Ile  Leu Asn Ile Gly Asn  Val Ser Thr
    2285             2290             2295

Pro Leu  Met Cys Leu Ser Glu  Ser Thr Asn Ser Thr  Glu Arg Asn
    2300             2305             2310

Val Met  Trp Gly Gly Cys Gly  Thr Lys Ile Phe Ser  Phe Ser Asn
    2315             2320             2325

Asp Phe  Thr Ile Gln Lys Leu  Ile Glu Thr Arg Thr  Ser Gln Leu
    2330             2335             2340

Phe Ser  Tyr Ala Ala Phe Ser  Asp Ser Asn Ile Ile  Thr Val Val
    2345             2350             2355

Val Asp  Thr Ala Leu Tyr Ile  Ala Lys Gln Asn Ser  Pro Val Val
    2360             2365             2370

Glu Val  Trp Asp Lys Lys Thr  Glu Lys Leu Cys Gly  Leu Ile Asp
    2375             2380             2385

Cys Val  His Phe Leu Arg Glu  Val Met Val Lys Glu  Asn Lys Glu
    2390             2395             2400

Ser Lys  His Lys Met Ser Tyr  Ser Gly Arg Val Lys  Thr Leu Cys
    2405             2410             2415

Leu Gln  Lys Asn Thr Ala Leu  Trp Ile Gly Thr Gly  Gly Gly His
    2420             2425             2430

Ile Leu  Leu Leu Asp Leu Ser  Thr Arg Arg Leu Ile  Arg Val Ile
    2435             2440             2445

Tyr Asn  Phe Cys Asn Ser Val  Arg Val Met Met Thr  Ala Gln Leu
    2450             2455             2460

Gly Ser  Leu Lys Asn Val Met  Leu Val Leu Gly Tyr  Asn Arg Lys
    2465             2470             2475

Asn Thr  Glu Gly Thr Gln Lys  Gln Lys Glu Ile Gln  Ser Cys Leu
    2480             2485             2490

Thr Val  Trp Asp Ile Asn Leu  Pro His Glu Val Gln  Asn Leu Glu
    2495             2500             2505

Lys His  Ile Glu Val Arg Lys  Glu Leu Ala Glu Lys  Met Arg Arg
    2510             2515             2520

Thr Ser  Val Glu
    2525
```

-continued

```
<210> SEQ ID NO 2
<211> LENGTH: 7584
<212> TYPE: DNA
<213> ORGANISM: Homo sapiens

<400> SEQUENCE: 2
atggctagtg gcagctgtca ggggtgcgaa gaggacgagg aaactctgaa gaagttgata      60
gtcaggctga acaatgtcca ggaaggaaaa cagatagaaa cgctggtcca aatcctggag     120
gatctgctgg tgttcacgta ctccgagcgc gcctccaagt tatttcaagg caaaaatatc     180
catgtgcctc tgttgatcgt cttggactcc tatatgagag tcgcgagtgt gcagcaggtg     240
ggttggtcac ttctgtgcaa attaatagaa gtctgtccag gtacaatgca aagcttaatg     300
ggaccccagg atgttggaaa tgattgggaa gtccttggtg ttcaccaatt gattcttaaa     360
atgctaacag ttcataatgc cagtgtaaac ttgtcagtga ttggactgaa gaccttagat     420
ctcctcctaa cttcaggtaa aatcaccttg ctgatattgg atgaagaaag tgatattttc     480
atgttaattt ttgatgccat gcactcattt ccagccaatg atgaagtcca gaaacttgga     540
tgcaaagctt tacatgtgct gtttgagaga gtctcagagg agcaactgac tgaatttgtt     600
gagaacaaag attatatgat attgttaagt gcgttaacaa attttaaaga tgaagaggaa     660
attgtgcttc atgtgctgca ttgtttacat tccctagcga ttccttgcaa taatgtggaa     720
gtcctcatga gtggcaatgt caggtgttat aatattgtgg tggaagctat gaaagcattc     780
cctatgagtg aaagaattca agaagtgagt tgctgtttgc tccataggct tacattaggt     840
aattttttca atatcctggt attaaacgaa gtccatgagt ttgtggtgaa agctgtgcag     900
cagtacccag agaatgcagc attgcagatc tcagcgctca gctgtttggc cctcctcact     960
gagactattt tcttaaatca agatttagag gaaaagaatg agaatcaaga gaatgatgat    1020 gaggggggaag aagataaatt gttttggctg gaagcctgtt acaaagcatt aacgtggcat    1080
agaaagaaca gcacgtgca ggaggccgca tgctgggcac taaataatct ccttatgtac     1140
caaaacagtt tacatgagaa gattggagat gaagatggcc atttcccagc tcatagggaa    1200
gtgatgctct ccatgctgat gcattcttca tcaaaggaag ttttccaggc atctgcgaat    1260
gcattgtcaa ctctcttaga acaaaatgtt aatttcagaa aaatactgtt atcaaaagga    1320
atacacctga atgttttgga gttaatgcag aagcatatac attctcctga agtggctgaa    1380
agtggctgta aaatgctaaa tcatcttttt gaaggaagca acacttccct ggatataatg    1440
gcagcagtgg tccccaaaat actaacagtt atgaaacgtc atgagacatc attaccagtg    1500
cagctggagg cgcttcgagc tattttacat tttatagtgc ctggcatgcc agaagaatcc    1560
agggaggata cagaatttca tcataagcta aatatggtta aaaaacagtg tttcaagaat    1620
gatattcaca aactggtcct agcagctttg aacaggttca ttggaaatcc tgggattcag    1680
aaatgtggat taaaagtaat ttcttctatt gtacattttc ctgatgcatt agagatgtta    1740
tccctggaag gtgctatgga ttcagtgctt cacacactgc agatgtatcc agatgaccaa    1800
gaaattcagt gtctgggttt aagtcttata ggatacttga ttacaaagaa gaatgtgttc    1860
ataggaactg acatctgct ggcaaaaatt ctggtttcca gcttataccg atttaaggat    1920
gttgctgaaa tacagactaa aggatttcag acaatcttag caatcctcaa attgtcagca    1980 tcttttttcta agctgctggt gcatcattca tttgacttag taatattcca tcaaatgtct    2040
tccaatatca tggaacaaaa ggatcaacag tttctaaacc tctgttgcaa gtgttttgca    2100
aaagtagcta tggatgatta cttaaaaaat gtgatgctag agagagcgtg tgatcagaat    2160
```

```
aacagcatca tggttgaatg cttgcttcta ttgggagcag atgccaatca agcaaaggag      2220
ggatcttctt taatttgtca ggtatgtgag aaagagagca gtcccaaatt ggtggaactc      2280
ttactgaata gtggatctcg tgaacaagat gtacgaaaag cgttgacgat aagcattggg      2340
aaaggtgaca gccagatcat cagcttgctc ttaaggaggc tggccctgga tgtggccaac      2400
aatagcattt gccttggagg attttgtata ggaaaagttg aaccttcttg cttggtcct       2460 ttatttccag ataagacttc taatttaagg aaacaaacaa atatagcatc tacactagca      2520
agaatggtga tcagatatca gatgaaaagt gctgtggaag aaggaacagc ctcaggcagc      2580
gatggaaatt tttctgaaga tgtgctgtct aaatttgatg aatggacctt tattcctgac      2640
tcttctatgg acagtgtgtt tgctcaaagt gatgacctgg atagtgaagg aagtgaaggc      2700
tcatttcttg tgaaaaagaa atctaattca attagtgtag gagaatttta ccgagatgcc      2760
gtattacagc gttgctcacc aaatttgcaa agacattcca attccttggg gcccattttt      2820
gatcatgaag atttactgaa gcgaaaaaga aaaatattat cttcagatga ttcactcagg      2880
tcatcaaaac ttcaatccca tatgaggcat tcagacagca tttcttctct ggcttctgag      2940
agagaatata ttcatcacact agacctttca gcaaatgaac taagagatat tgatgccta       3000 agccagaaat gctgtataag tgttcatttg gagcatcttg aaaagctgga gcttcaccag      3060
aatgcactca cgagctttcc acaacagcta tgtgaaactc tgaagagttt gacacatttg      3120
gacttgcaca gtaataaatt tacatcattt ccttcttatt tgttgaaaat gagttgtatt      3180
gctaatcttg atgtctctcg aaatgacatt ggaccctcag tggttttaga tcctacagtg      3240
aaatgtccaa ctctgaaaca gtttaacctg tcatataacc agctgtcttt tgtacctgag      3300
aacctcactg atgtggtaga gaaactggag cagctcattt tagaaggaaa taaaatatca      3360
gggatatgct cccccttgag actgaaggaa ctgaagattt taaaccttag taagaaccac      3420
atttcatccc tatcagagaa ctttcttgag gcttgtccta aagtggagag tttcagtgcc      3480
agaatgaatt ttcttgctgc tatgcctttc ttgcctcctt ctatgacaat cctaaaatta      3540
tctcagaaca aattttcctg tattccagaa gcaattttaa atcttccaca cttgcggtct      3600
ttagatatga gcagcaatga tattcagtac ctaccaggtc ccgcacactg gaaatctttg      3660
aacttaaggg aactcttatt tagccataat cagatcagca tcttggactt gagtgaaaaa      3720
gcatatttat ggtctagagt agagaaactg catctttctc acaataaact gaaagagatt      3780
cctcctgaga ttggctgtct tgaaaatctg acatctctgg atgtcagtta caacttggaa      3840
ctaagatcct ttcccaatga aatgggggaaa ttaagcaaaa tatgggatct tcctttggat      3900
gaactgcatc ttaactttga ttttaaacat ataggatgta aagccaaaga catcataagg      3960
tttcttcaac agcgattaaa aaaggctgtg ccttataacc gaatgaaact tatgattgtg      4020
ggaaatactg ggagtggtaa aaccacctta ttgcagcaat aatgaaaac caagaaatca       4080 gatcttggaa tgcaaagtgc cacagttggc atagatgtga aagactggcc tatccaaata      4140
agagacaaaa gaaagagaga tctcgtccta aatgtgtggg attttgcagg tcgtgaggaa      4200
ttctatagta ctcatcccca tttttatgacg cagcgagcat tgtaccttgc tgtctatgac      4260
ctcagcaagg gacaggctga agttgatgcc atgaagcctt ggctcttcaa tataaaggct      4320
cgcgcttctt cttcccctgt gattctcgtt ggcacacatt tggatgtttc tgatgagaag      4380
caacgcaaag cctgcatgag taaaatcacc aaggaactcc tgaataagcg agggttccct      4440
gccatacgag attaccactt tgtgaatgcc accgaggaat ctgatgcttt ggcaaaactt      4500
```

-continued

```
cggaaaacca tcataaacga gagccttaat ttcaagatcc gagatcagct tgttgttgga        4560
cagctgattc cagactgcta tgtagaactt gaaaaaatca ttttatcgga gcgtaaaaat        4620
gtgccaattg aatttcccgt aattgaccgg aaacgattat tacaactagt gagagaaaat        4680
cagctgcagt tagatgaaaa tgagcttcct cacgcagttc actttctaaa tgaatcagga        4740
gtccttcttc attttcaaga cccagcactg cagttaagtg acttgtactt tgtggaaccc        4800
aagtggcttt gtaaaatcat ggcacagatt ttgacagtga aagtggaagg ttgtccaaaa        4860
caccctaagg gcattatttc gcgtagagat gtggaaaaat ttctttcaaa aaaaaggaaa        4920
tttccaaaga actacatgtc acagtatttt aagctcctag aaaaattcca gattgctttg        4980
ccaataggag aagaatattt gctggttcca agcagtttgt ctgaccacag gcctgtgata        5040
gagcttcccc attgtgagaa ctctgaaatt atcatccgac tatatgaaat gccttatttt        5100
ccaatgggat tttggtcaag attaatcaat cgattacttg agatttcacc ttacatgctt        5160
tcagggagag aacgagcact tcgcccaaac agaatgtatt ggcgacaagg catttactta        5220
aattggtctc ctgaagctta ttgtctggta ggatctgaag tcttagacaa tcatccagag        5280
agtttcttaa aaattacagt tccttcttgt agaaaaggct gtattctttt gggccaagtt        5340
gtggaccaca ttgattctct catggaagaa tggtttcctg ggttgctgga gattgatatt        5400
tgtggtgaag gagaaactct gttgaagaaa tgggcattat atagtttta tgatggtgaa        5460 gaacatcaaa aaatcttact tgatgacttg atgaagaaag cagaggaagg agatctctta        5520
gtaaatccag atcaaccaag gctcaccatt ccaatatctc agattgcccc tgacttgatt        5580
ttggctgacc tgcctagaaa tattatgttg aataatgatg agttggaatt tgaacaagct        5640
ccagagtttc tcctaggtga tggcagtttt ggatcagttt accgagcagc ctatgaagga        5700
gaagaagtgg ctgtgaagat ttttaataaa catacatcac tcaggctgtt aagacaagag        5760
cttgtggtgc tttgccacct ccaccacccc agtttgatat ctttgctggc agctgggatt        5820
cgtcccggga tgttggtgat ggagttagcc tccaagggtt ccttggatcg cctgcttcag        5880
caggacaaag ccagcctcac tagaaaccct agcacagga ttgcactcca cgtagctgat        5940
ggtttgagat acctccactc agccatgatt atataccgag acctgaaacc ccacaatgtg        6000
ctgcttttca cactgtatcc caatgctgcc atcattgcaa agattgctga ctacggcatt        6060
gctcagtact gctgtagaat ggggataaaa acatcagagg gcacaccagg gtttcgtgca        6120
cctgaagttg ccagaggaaa tgtcatttat aaccaacagg ctgatgttta ttcatttggt        6180
ttactactct atgacatttt gacaactgga ggtagaatag tagagggttt gaagtttcca        6240
aatgagtttg atgaattaga aatacaagga aaattacctg atccagttaa agaatatggt        6300
tgtgccccat ggcctatggt tgagaaatta attaaacagt gtttgaaaga aaatcctcaa        6360
gaaaggccta cttctgccca ggtctttgac attttgaatt cagctgaatt agtctgtctg        6420
acgagacgca ttttattacc taaaaacgta attgttgaat gcatggttgc tacacatcac        6480
aacagcagga atgcaagcat ttggctgggc tgtgggcaca ccgacagagg acagctctca        6540
tttcttgact taaatactga aggatacact tctgaggaag ttgctgatag tagaatattg        6600
tgcttagcct tggtgcatct tcctgttgaa aaggaaagct ggattgtgtc tgggacacag        6660
tctggtactc tcctggtcat caataccgaa gatgggaaaa agagacatac cctagaaaag        6720
atgactgatt ctgtcacttg tttgtattgc aattcctttt ccaagcaaag caaacaaaaa        6780
aattttcttt tggttggaac cgctgatggc aagttagcaa ttttttgaaga taagactgtt        6840 aagcttaaag gagctgctcc tttgaagata ctaaatatag gaaatgtcag tactccattg        6900
```

-continued

```
atgtgtttga gtgaatccac aaattcaacg gaaagaaatg taatgtgggg aggatgtggc    6960
acaaagattt tctcctttttc taatgatttc accattcaga aactcattga gacaagaaca    7020
agccaactgt tttcttatgc agctttcagt gattccaaca tcataacagt ggtggtagac    7080
actgctctct atattgctaa gcaaaatagc cctgttgtgg aagtgtggga taagaaaact    7140
gaaaaactct gtggactaat agactgcgtg cactttttaa gggaggtaat ggtaaaagaa    7200
aacaaggaat caaaacacaa aatgtcttat tctgggagag tgaaaaccct ctgccttcag    7260
aagaacactg ctctttggat aggaactgga ggaggccata ttttactcct ggatctttca    7320
actcgtcgac ttatacgtgt aatttacaac ttttgtaatt cggtcagagt catgatgaca    7380
gcacagctag gaagccttaa aaatgtcatg ctggtattgg gctacaaccg gaaaaatact    7440
gaaggtacac aaaagcagaa agagatacaa tcttgcttga ccgtttggga catcaatctt    7500
ccacatgaag tgcaaaattt agaaaaacac attgaagtga gaaaagaatt agctgaaaaa    7560
atgagacgaa catctgttga gtaa                                         7584
```

What is claimed is:

1. A method of treating invasive breast cancer in a subject, the method comprising:
   (a) obtaining a biological sample from the subject having invasive breast cancer;
   (b) determining, in the sample, the presence of one or more inactivating LRRK2 mutations in a LRRK2 gene or a LRRK2 protein, wherein the one or more inactivating mutations in the LRRK2 gene are located in the coding sequence for one or more of the following domains of the LRRK2 protein: the Armadillo domain, inter-domain, leucine-rich repeat ROC domain, kinase domain, or WD40 domain, wherein the one or more inactivating mutations in the LRRK2 gene are one or more of a missense mutation, a frameshift mutation, or a nonsense mutation, and wherein the one or more inactivating mutations in the LRRK2 gene or the LRRK2 protein consist of one or more of the following mutations: c.1274T>C, c.1605del, c.2573C>G, c.2765T>A, c.3266A>G, c.4469C>T, c.3910C>T, c.4334C>T, c.4514_4520del, c.4915dup, c.5072T>C, c.5117C>G, c.5312G>C, c.5455G>C, c.5861C>T, c.6322G>A, c.7153G>A, p.L425P, p.K535Nfs*13, p.S858*, p.L922*, p.N1089S, p.A1490V, p.L1304F, p.S1445F, p.I1505Rfs*16, p.R1639Kfs*13, p.I1691T, p.S1706*, p.R1771T, p.G1819R, p.S1954F, p.E2108K, or p.G2385R; and
   (c) administering, to the subject having the one or more inactivating mutations in the LRRK2 gene or the LRRK2 protein, a therapeutically effective amount of an immune checkpoint therapy, wherein the immune checkpoint therapy is at least one of a programmed death-1 (PD-1) inhibitor, a programmed death-ligand 1 (PD-L1) inhibitor, a cytotoxic T-lymphocyte associated antigen 4 (CTLA-4) inhibitor, a T-cell immunoglobulin and mucin-domain containing-3 (TIM3) inhibitor, a B and T lymphocyte attenuator (BTLA) inhibitor, a V-domain immunoglobulin suppressor of T cell activation (VISTA) receptor inhibitor, a lymphocyte activation gene 3 (LAG3) inhibitor, or a combination thereof.

2. The method of claim 1, wherein the method further comprises administering one or more additional therapies to treat the invasive breast cancer.

3. The method of claim 2, wherein the one or more additional therapies comprises one or more of chemotherapy, radiation, surgery, or combinations thereof.

4. The method of claim 3, wherein the one or more additional therapies is administered prior to the immune checkpoint therapy.

5. The method of claim 3, wherein the one or more additional therapies is administered concurrently with the immune checkpoint therapy.

6. The method of claim 3, wherein the one or more additional therapies is administered after the immune checkpoint therapy.

7. A method of treating a subject with invasive breast cancer, comprising:
   selecting a subject with invasive breast cancer that has one or more inactivating mutations in a LRRK2 gene or a LRRK2 protein, wherein the one or more inactivating mutations in the LRRK2 gene are located in the coding sequence of one or more of the following domains of the LRRK2 protein: the Armadillo domain, inter-domain, leucine-rich repeat ROC domain, kinase domain, or WD40 domain, and wherein the one or more inactivating mutations in the LLRK2 gene are one or more of a missense mutation, a frameshift mutation, or a nonsense mutation, and wherein the one or more inactivating mutations in the LRRK2 gene or the LRRK2 protein consist of one or more of the following mutations: c.1274T>C, c.1605del, c.2573C>G, c.2765T>A, c.3266A>G, c.4469C>T, c.3910C>T, c.4334C>T, c.4514_4520del, c.4915dup, c.5072T>C, c.5117C>G, c.5312G>C, c.5455G>C, c.5861C>T, c.6322G>A, c.7153G>A, p.L425P, p.K535Nfs*13, p.S858*, p.L922*, p.N1089S, p.A1490V, p.L1304F, p.S1445F, p.I1505Rfs*16, p.R1639Kfs*13, p.I1691T, p.S1706*, p.R1771T, p.G1819R, p.S1954F, p.E2108K, or p.G2385R; and
   administering a therapeutically effective amount of an immune checkpoint therapy to the subject, wherein the immune checkpoint therapy is at least one of a programmed death-1 (PD-1) inhibitor, a programmed death-ligand 1 (PD-L1) inhibitor, a cytotoxic T-lymphocyte associated antigen 4 (CTLA-4) inhibitor, a T-cell immunoglobulin and mucin-domain containing-3 (TIM3) inhibitor, a B and T lymphocyte attenuator (BTLA) inhibitor, a V-domain immunoglobulin suppressor of T cell activation (VISTA) receptor inhibitor, a lymphocyte activation gene 3 (LAG3) inhibitor, or a combination thereof.

8. The method of claim 7, wherein the method further comprises administering one or more additional therapies to the subject to treat the invasive breast cancer.

9. The method of claim 7, wherein the one or more additional therapies comprises one or more of chemotherapy, radiation, surgery, or combinations thereof.

10. The method of claim 8, wherein the one or more additional therapies is administered prior to the immune checkpoint therapy.

11. The method of claim 8, wherein the one or more additional therapies is administered concurrently with the immune checkpoint therapy.

12. The method of claim 8, wherein the one or more additional therapies is administered after the immune checkpoint therapy.

\* \* \* \* \*